(12) United States Patent
Roush et al.

(10) Patent No.: US 9,125,633 B2
(45) Date of Patent: Sep. 8, 2015

(54) DEVICE FOR MIXING AND DISPENSING OF TWO-COMPONENT REACTIVE SURGICAL SEALANT

(75) Inventors: Daniel E. Roush, Niles, IL (US); Justin Stevens, Vienna (AT); Atif M. Yardimci, Lake Forest, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 823 days.

(21) Appl. No.: 13/342,271

(22) Filed: Jan. 3, 2012

(65) Prior Publication Data

US 2012/0158048 A1 Jun. 21, 2012

Related U.S. Application Data

(63) Continuation-in-part of application No. 12/823,786, filed on Jun. 25, 2010, now Pat. No. 8,672,237.

(51) Int. Cl.
*A61B 17/00* (2006.01)
*B01F 5/00* (2006.01)
(Continued)

(52) U.S. Cl.
CPC ......... *A61B 17/00491* (2013.01); *B01F 5/0057* (2013.01); *B01F 13/0023* (2013.01);
(Continued)

(58) Field of Classification Search
CPC .............. A61B 17/00491; B01F 13/0023; B01F 15/0087; B01F 5/0057; B05B 11/0078; B05B 7/0416
USPC ............... 236/398, 400, 428, 490, 491, 493; 604/39, 40, 43, 57, 58, 60, 82–92, 604/93.01, 181, 187, 191, 236, 258, 264, 604/266, 523–528; 222/135–137, 145.5, 222/145.6; 606/213, 214
See application file for complete search history.

(56) References Cited

U.S. PATENT DOCUMENTS 3,169,528 A * 2/1965 Knox, III et al. ............. 604/532
4,359,049 A * 11/1982 Redl et al. ........................ 604/82
(Continued)

FOREIGN PATENT DOCUMENTS

DE 29516077 U1 2/1997
EP 2111918 A2 10/2009
(Continued)

OTHER PUBLICATIONS

International Preliminary Report on Patentability for corresponding International Application No. PCT/US11/41720, dated Dec. 28, 2012.
(Continued)

*Primary Examiner* — Ryan Reis
*Assistant Examiner* — Chee-Chong Lee
(74) *Attorney, Agent, or Firm* — Marshall, Gerstein & Borun LLP

(57) ABSTRACT

An applicator for mixing and applying multi-component compositions to a work surface, such as two-component surgical sealants. A luer hub sub-assembly having a proximal hub and a distal hub, an elongate, four-lumened cannula, and a spray tip sub-assembly are provided, with interconnections between the sub-assemblies preserving isolation of the fluid components from one another. The tip cap sub-assembly includes registration structure to assure proper alignment between tip cap and tip insert. The end wall of the tip cap includes a spinner region with three feeders or feeder channels leading thereto, the fluid components remaining isolated from one another in two of the feeders or feeder channels, and initiating mixing with one another in a third of the feeders or feeder channels.

14 Claims, 12 Drawing Sheets

(51) Int. Cl.
*B01F 13/00* (2006.01)
*B01F 15/00* (2006.01)
*B05B 1/34* (2006.01)
*B05B 7/04* (2006.01)
*B05B 9/08* (2006.01)
*B05B 11/00* (2006.01)
*B05B 11/02* (2006.01)
*A61B 19/00* (2006.01)
*B01F 15/02* (2006.01)
*B05B 1/04* (2006.01)

(52) U.S. Cl.
CPC ........... *B01F15/0087* (2013.01); *B05B 1/3436* (2013.01); *B05B 7/0408* (2013.01); *B05B 9/0838* (2013.01); *B05B 11/0078* (2013.01); *B05B 11/02* (2013.01); *A61B 19/5212* (2013.01); *A61B 2017/00495* (2013.01); *A61B 2017/00951* (2013.01); *A61B 2019/5206* (2013.01); *B01F 2015/0221* (2013.01); *B05B 1/04* (2013.01)

(56) References Cited

U.S. PATENT DOCUMENTS

| | | | |
|---|---|---|---|
| 4,874,368 A * | 10/1989 | Miller et al. | 604/82 |
| 4,978,336 A * | 12/1990 | Capozzi et al. | 604/82 |
| 5,116,315 A | 5/1992 | Capozzi et al. | |
| 5,417,208 A * | 5/1995 | Winkler | 600/374 |
| 5,454,795 A * | 10/1995 | Samson | 604/526 |
| 5,605,255 A | 2/1997 | Reidel et al. | |
| 5,740,965 A * | 4/1998 | Miyagi et al. | 239/423 |
| 5,810,885 A * | 9/1998 | Zinger | 606/213 |
| 5,874,500 A | 2/1999 | Rhee et al. | |
| 6,161,730 A * | 12/2000 | Heusser et al. | 222/137 |
| 6,165,201 A * | 12/2000 | Sawhney et al. | 606/214 |
| 6,312,725 B1 | 11/2001 | Wallace et al. | |
| 6,328,229 B1 | 12/2001 | Duronio et al. | |
| 6,461,325 B1 * | 10/2002 | Delmotte et al. | 604/82 |
| 6,783,514 B2 * | 8/2004 | Tovey et al. | 604/191 |
| 6,884,232 B1 * | 4/2005 | Hagmann et al. | 604/82 |
| 2010/0065660 A1 * | 3/2010 | Hull et al. | 239/428 |
| 2011/0319930 A1 | 12/2011 | Roush et al. | |

FOREIGN PATENT DOCUMENTS

| | | |
|---|---|---|
| RU | 2008109806 A | 9/2009 |
| SU | 704609 A1 | 12/1979 |
| SU | 705266 A1 | 12/1979 |
| SU | 1809761 | 4/1993 |
| WO | WO-2010/042341 A1 | 4/2010 |

OTHER PUBLICATIONS

International Search Report and Written Opinion for corresponding international application No. PCT/US2011/041720, mailing date May 24, 2012.

COSEAL® Surgical Sealant, Instructions for Use, Baxter Healthcare Corporation, Rev. Mar. 2009.

* cited by examiner

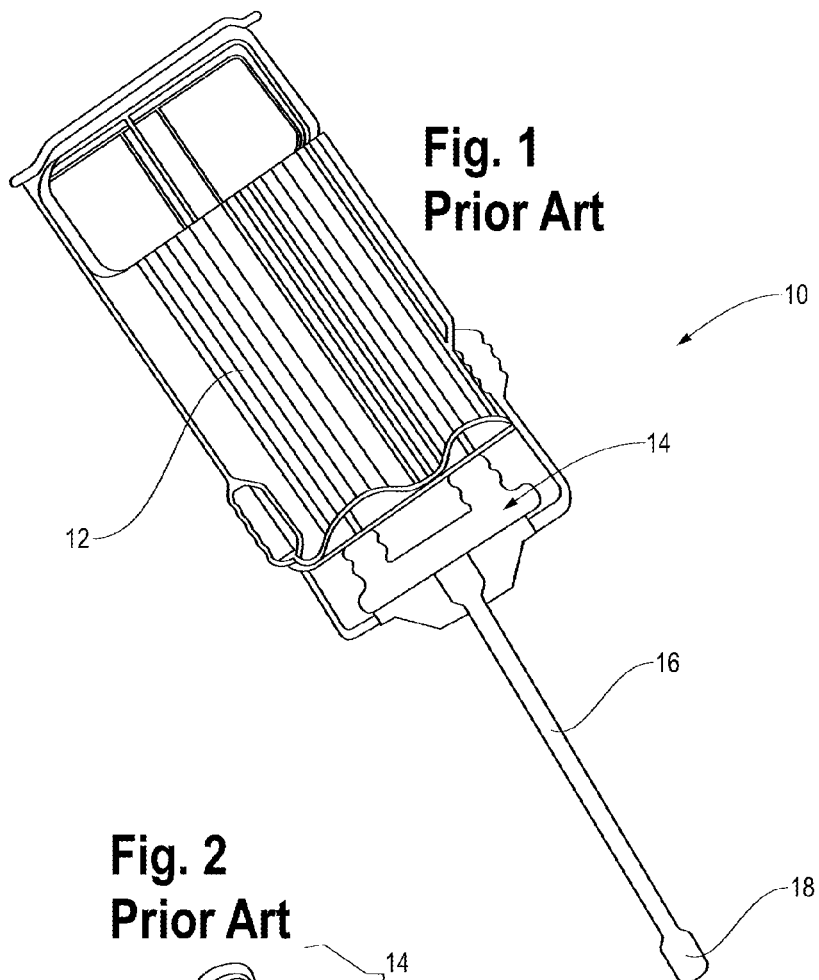
Fig. 1
Prior Art
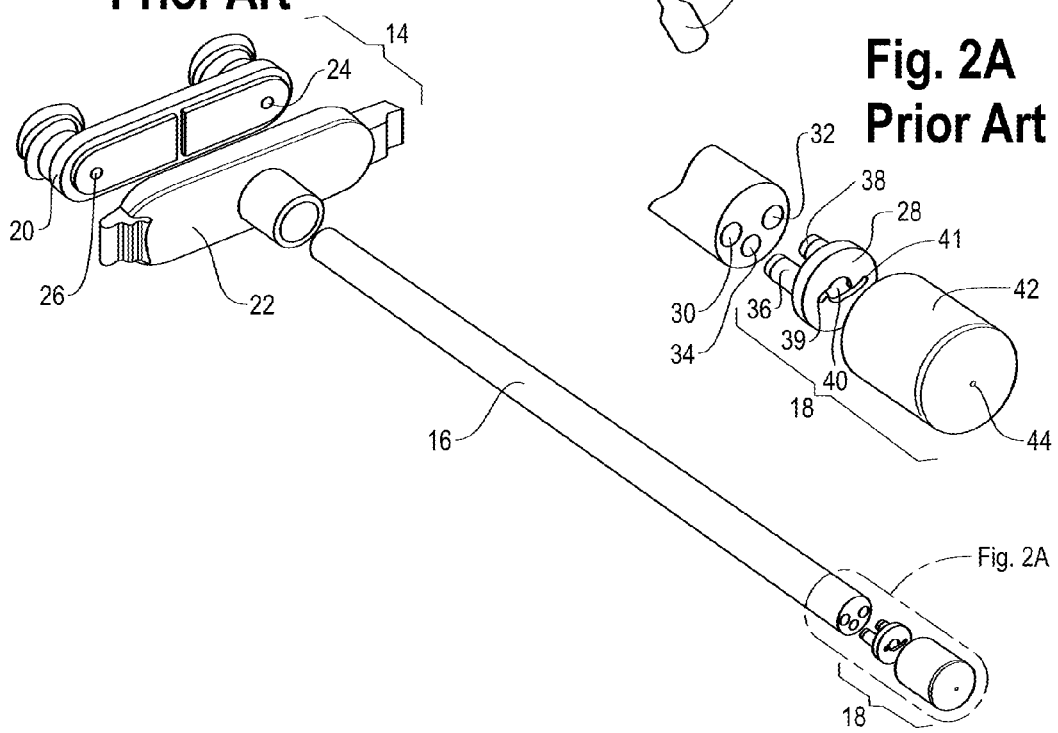
Fig. 2
Prior Art
Fig. 2A
Prior Art

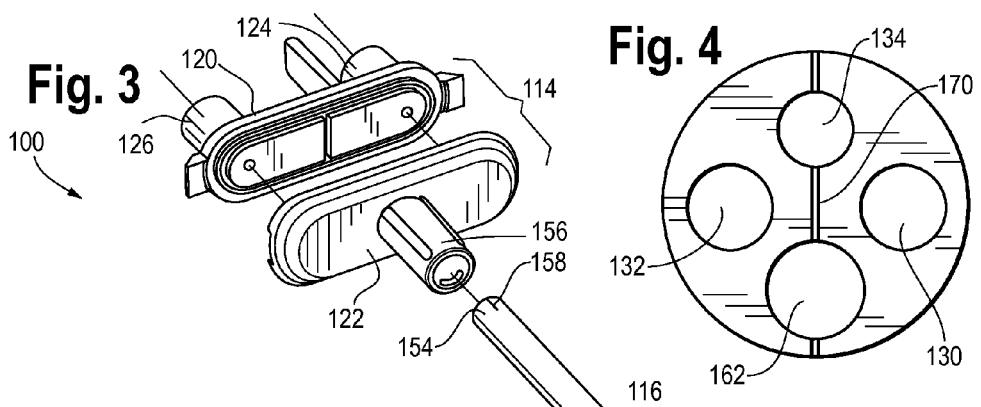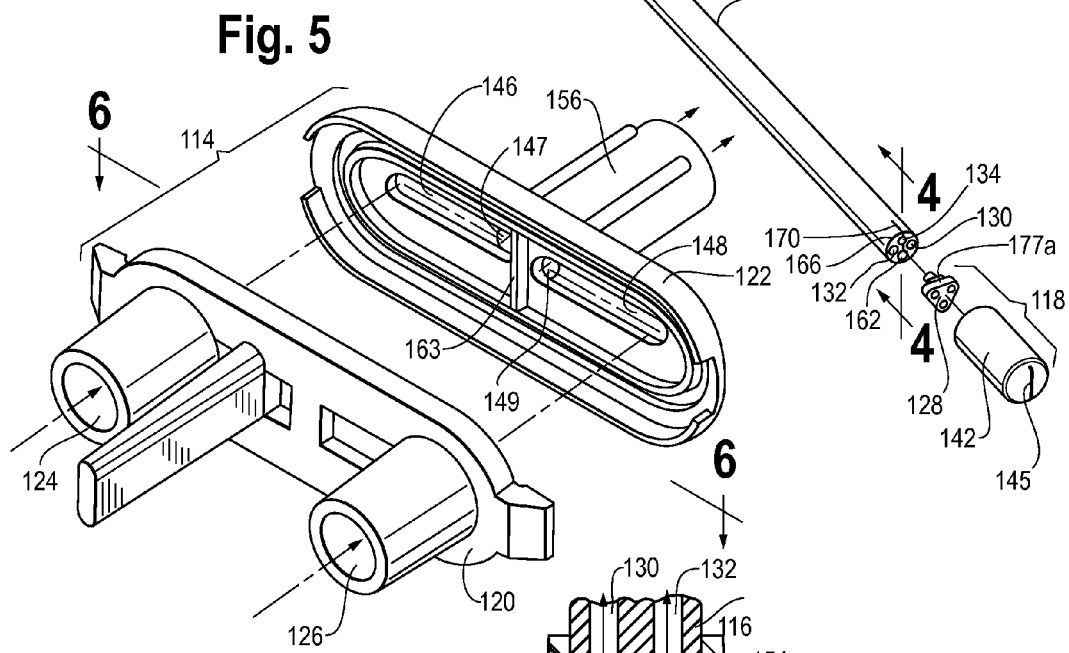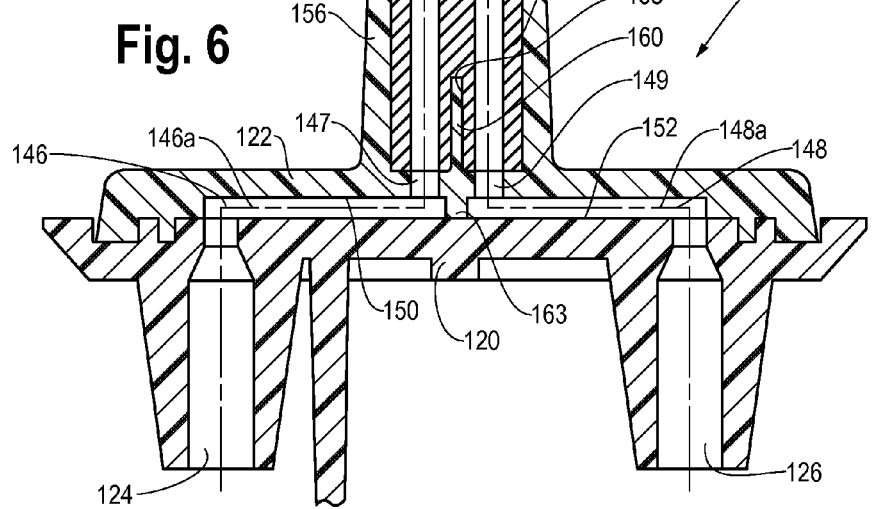

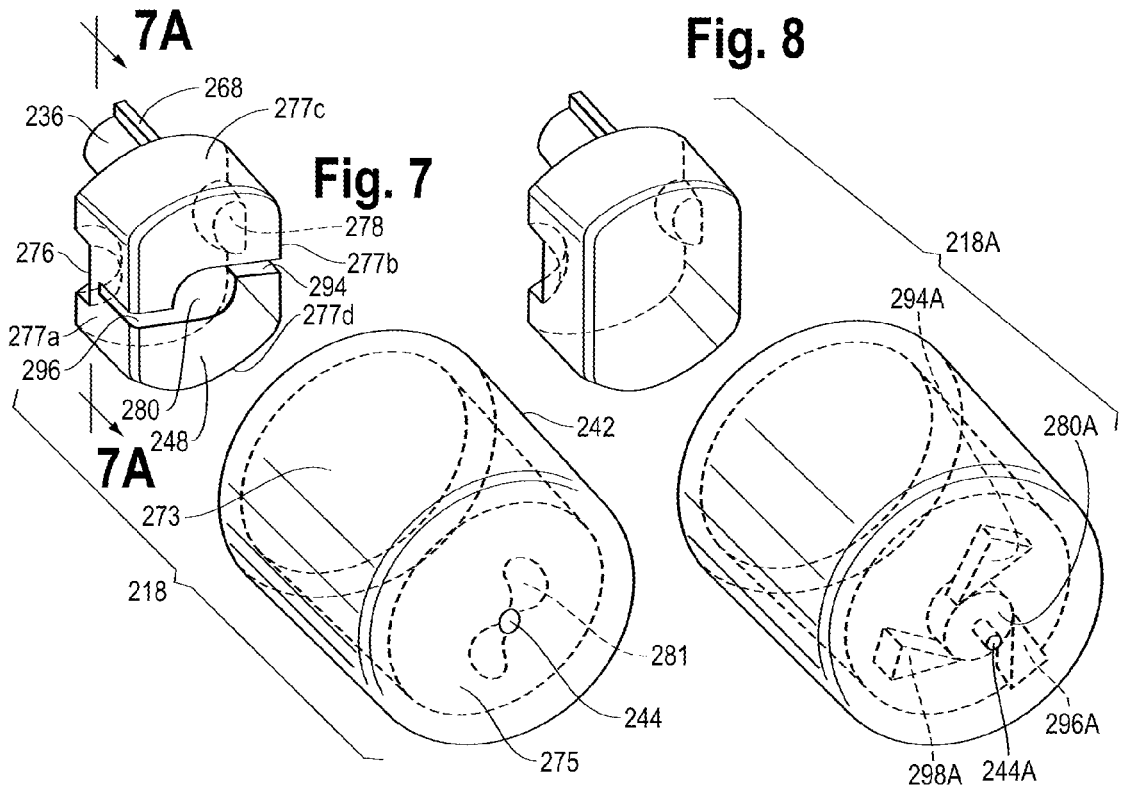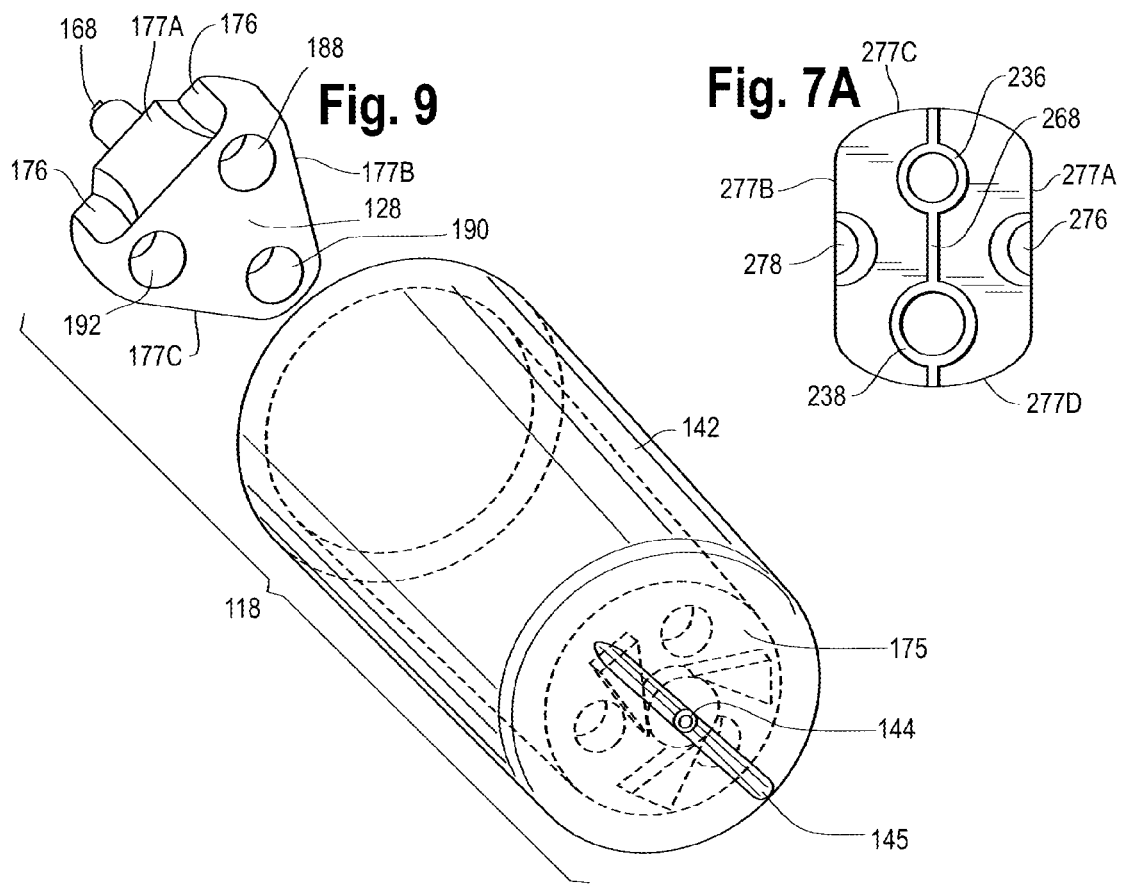

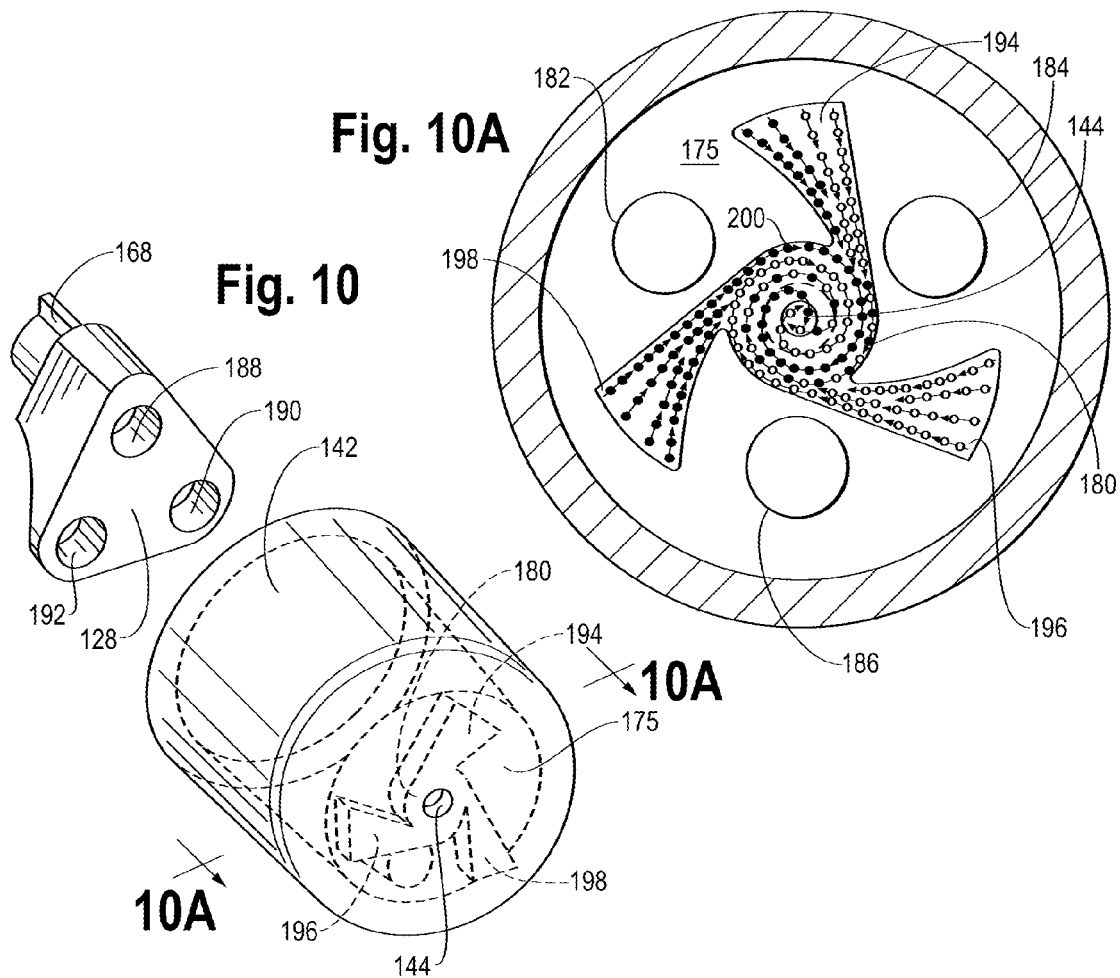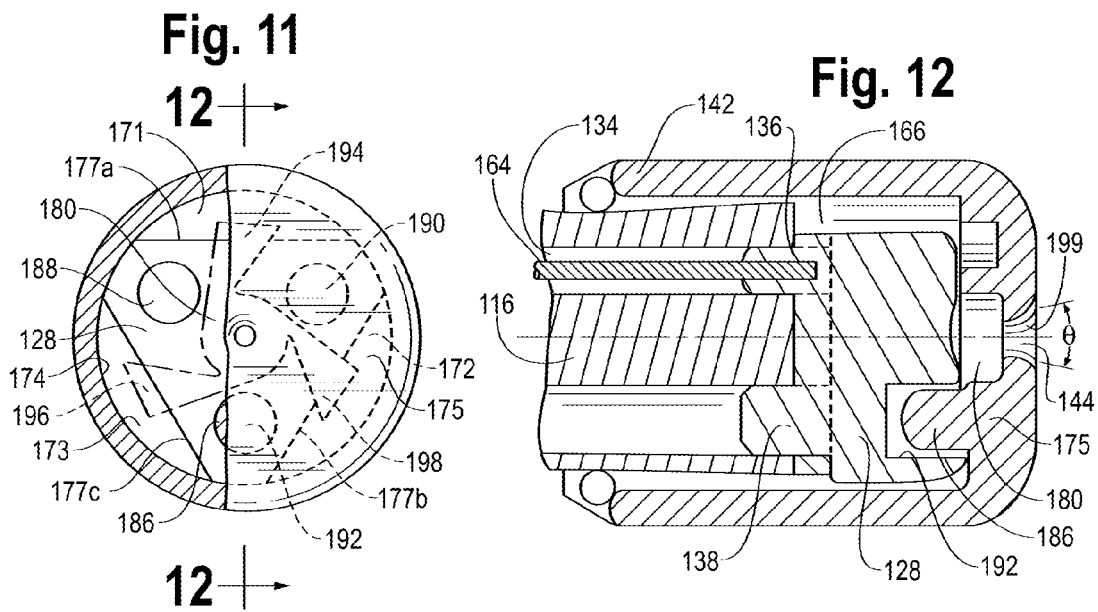

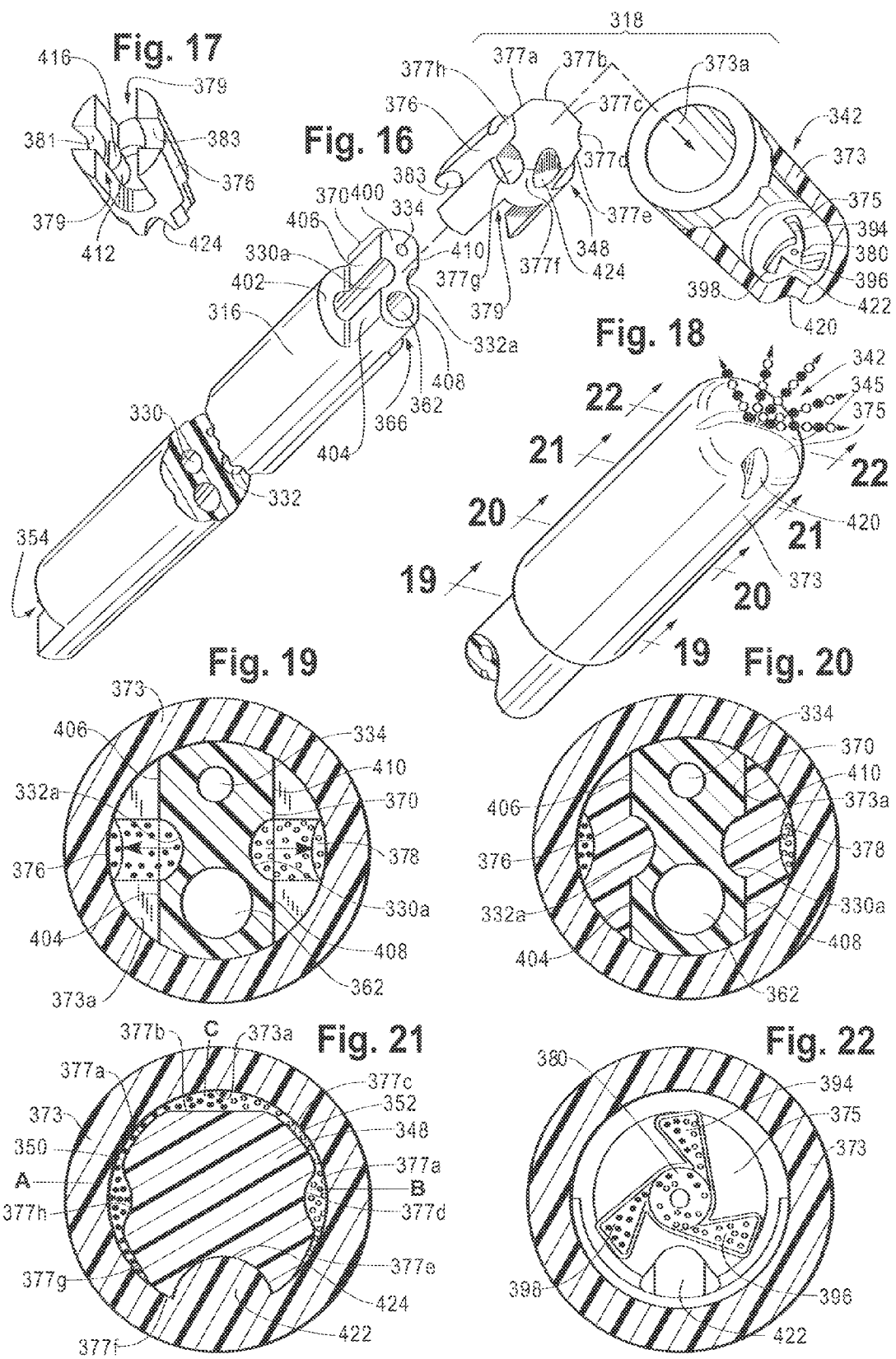

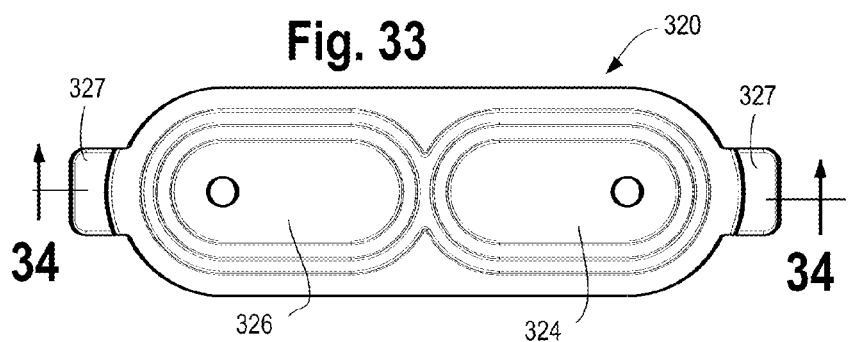
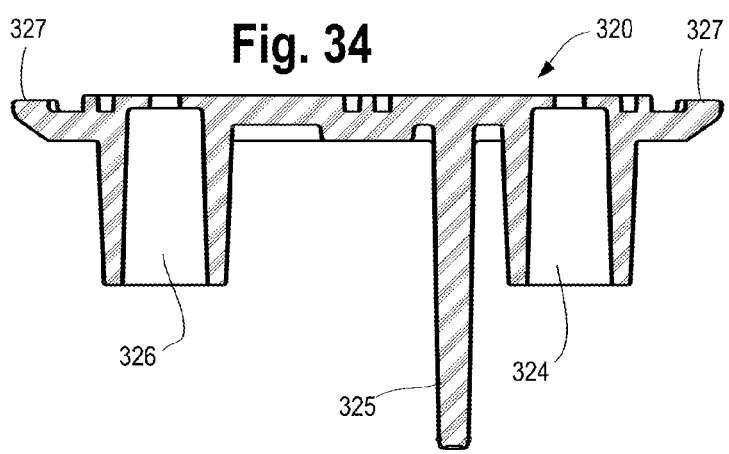
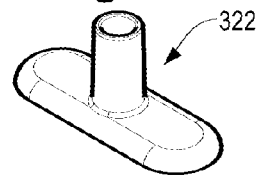
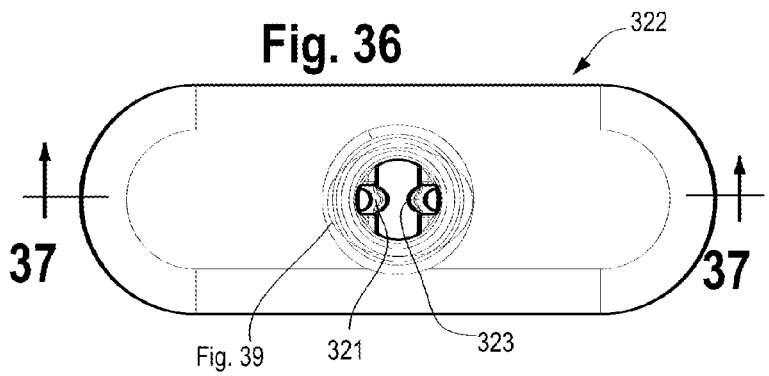
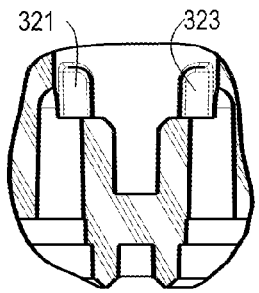
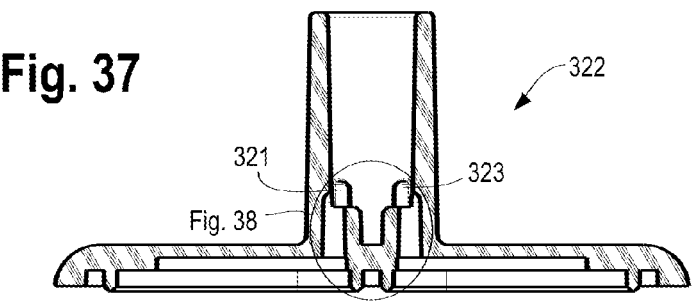
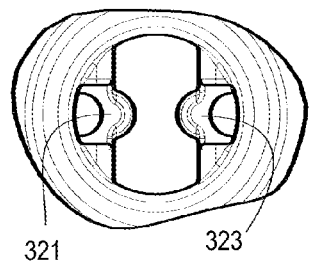

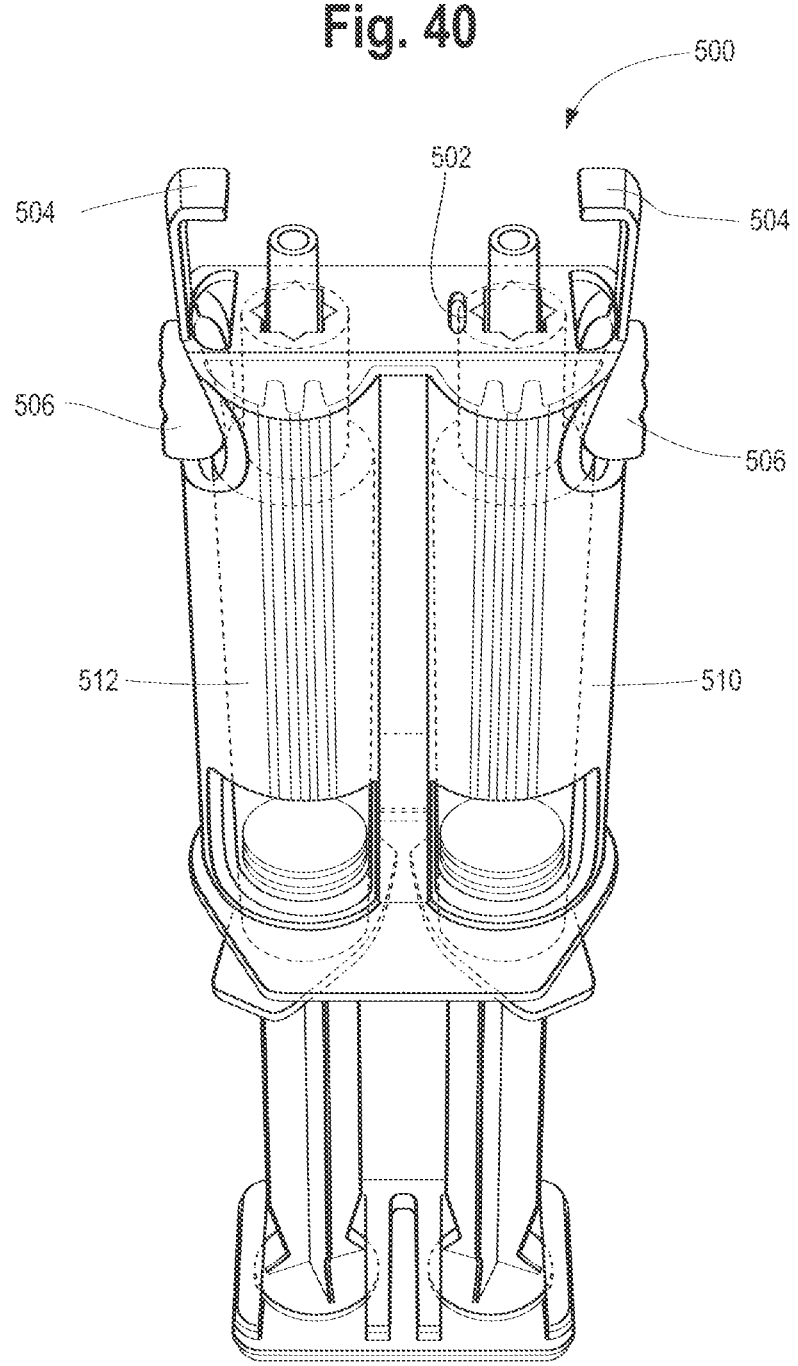

DEVICE FOR MIXING AND DISPENSING OF TWO-COMPONENT REACTIVE SURGICAL SEALANT

REFERENCE TO RELATED APPLICATIONS

This is a Continuation-in-Part of U.S. patent application Ser. No. 12/823,786, filed Jun. 25, 2010, the entirety of which is incorporated herein by reference.

FIELD OF THE DISCLOSURE

This disclosure relates generally to systems for applying a sealant to a work surface and, more particularly, to a device for mixing and applying a multi-component composition, such as a surgical tissue sealant made of two fluid components, to biological tissue employing structure that facilitates controlled spray application of the sealant.

BRIEF SUMMARY OF THE DISCLOSURE

The device of the present disclosure is particularly useful for mixing and applying multi-component compositions to a work surface, such as two-component surgical sealants, while avoiding clogs, preventing cross-contamination of the components until a point of intended mixing at a location within the apparatus in close proximity to an application opening in a tip cap, decreasing pressure drop along the apparatus and system to facilitate fluid delivery, and increasing efficiency of mixing of the components. It will be appreciated that not all of these advantages need be achieved by a mixing and dispensing device made in accordance with the present disclosure.

The mixing and dispensing device maintains a physical boundary between each component of a two-component composition until it is suitable to initiate contact, which is particularly desirable for components that quickly react upon exposure to one another. In the case of multi-part surgical sealants, the components, such as a buffer (e.g., a dilute hydrogen chloride solution) and a reconstituted mix of two synthetic polyethylene glycols (PEG's), begin to react with one another almost immediately upon exposure to each other, so it is desirable to avoid premature mixing, i.e. cross-contamination or "cross-talk" of the components, while they are within the mixing and dispensing device. It is also desirable to avoid inadequate mixing of components, as failure to adequately mix the components may yield a poor mixture and cause clogging, for example. Further, premixing a desired proportion of each of the components being mixed before all of the components are mixed together just prior to application results in an improved mixture.

The mixing and dispending device includes an applicator having three sub-assemblies, namely: a luer hub sub-assembly that docks or mates with a two-barreled syringe, also referred to herein as a dual syringe (one of the syringes carrying a buffer and the other syringe receiving a mix of two PEG's prior to engagement with the luer hub sub-assembly); a malleable cannula; and a spray tip sub-assembly. The luer hub sub-assembly includes a proximal hub and a distal hub. The malleable cannula is preferably formed as an extrusion of soft thermoplastic polyurethane elastomer, such as Pellethane™ (available from The Dow Chemical Company) and includes lumens therein, preferably four lumens. Two of the lumens carry fluid, with each of the fluid carrying lumens placed in fluid communication with a respective chamber or barrel of the dual syringe. One of the lumens carries a wire, preferably a dead soft, fully annealed wire, that is used to facilitate bending of the malleable cannula, but also helps to retain the malleable cannula in a position into which it is bent. The fourth lumen may be left vacant, serving primarily to maintain substantially constant wall thickness during extrusion of the malleable cannula, but could alternatively accommodate, by way of example only, vacuum pressure (i.e., suction), pressurized gas, flushing solution, a light, a heat source, or a fiber optic camera.

The spray tip sub-assembly includes a tip insert and a tip cap. The tip insert is provided with alignment posts that are received in apertures provided in the malleable cannula, such as in the wire-carrying lumen and in the vacant lumen. If the vacant lumen instead is serving to provide, for example, a vacuum, a pressurized gas, a flushing solution, or a light, the alignment post received therein may be hollow to accommodate such lumen-delivered services.

The tip cap has a spray opening therein, and a spinner region or spin chamber is embedded in an interior surface thereof, on the underside of the end in which the spray opening is provided. Indentations that serve as feeders or feeder channels to the spin chamber are also provided in the interior surface of the tip cap. Angled indentations of the tip insert direct flow to sides of the tip insert, then into the spinner region. The tip cap may be provided with mating pins that are received in complementary holes on a distal face of the tip insert, ensuring proper alignment of the spin chamber with the tip insert.

In one embodiment, a webbing is provided between the alignment posts of the tip insert, with a complementary slot provided in a mating end of the malleable cannula. The webbing helps to prevent cross-talk between a substantial portion of the fluid components in the two fluid-carrying lumens as the fluids flow from the malleable cannula into the tip insert. A similar webbing, alignment post, and complementary slot arrangement may be provided where the proximal hub of the luer hub sub-assembly mates with the malleable cannula. A solvent is preferably applied to the slots to bond the tip insert to the cannula. An adhesive may also be used for bonding purposes.

In another embodiment, the malleable cannula includes a pair of notches in each of the proximal and distal ends thereof, each of the notches exposing a semi-cylindrical channel region of a corresponding one of the fluid-carrying lumens. Each of the notches extends from an end wall of the malleable cannula (at which the non-fluid carrying lumens terminate) to a stop wall spaced axially inwardly of the end wall, thereby defining a male projection of the malleable cannula at each of the proximal and distal ends. Each of the semi-cylindrical channel regions of the fluid-carrying lumens exposed at the respective notch is bounded along its lateral edges by a pair of alignment ledges extending to the outer perimeter of the malleable cannula. In this embodiment, the tip insert of the tip cap sub-assembly is provided with a complementary female mating port to receive the male projection at the distal end of the malleable cannula. Once the male projection of the malleable cannula is engaged with the female mating port of the tip insert, each of a pair of fluid path archways of the tip insert is aligned with a portion of a respective one of the semi-cylindrical channel regions.

The tip insert further includes a pair of substantially Quonset-shaped wedges, each of which occupies a portion of a respective one of the semi-cylindrical channel regions closer to the end face of the tip cap, diverting fluid from the fluid-carrying lumens radially outward, through the fluid path archways, and into flow paths defined between crescent-shaped channels running axially along an exterior of the tip insert and an inner wall of the tip cap. Similar structure may be provided at the interface of the distal hub of the luer hub sub-assembly and the proximal end of the malleable cannula in order to direct fluid from the luer hub sub-assembly (to which a double-barreled syringe is selectively secured, such as with actuable locking tabs and clips) into the respective fluid-carrying lumens of the malleable cannula.

The crescent-shaped channels of the tip insert direct fluid from the fluid carrying channels of the malleable cannula toward an area between the walls of the tip insert and the tip cap, allowing a first mixing component only to be directed between an area between the tip insert and the tip cap, a second mixing component only to be directed between a separate and distinct area between the tip insert and the tip cap, and a combination of both the first and second mixing components to be directed between yet another separate, distinct area between the tip insert and the tip cap. Thus, a plurality of isolated flow paths are provided between the tip insert and the tip cap, with one of the flow paths including a mixture of both the first and second mixing components, while the other flow paths include either the first mixing component only or the second mixing component only.

In order to assure proper alignment between the tip cap and the tip insert, the tip cap may be provided with an inwardly-directed dimple or depression in a region of the tip cap where the sidewall of the tip cap meets the end wall of the tip cap, with a corresponding interior region of the tip cap having an inwardly-directed key. A complementary alignment notch is provided in a distal end of the tip insert, which receives the inwardly-directed key when the tip insert is received in the tip cap. To facilitate assembly of the various components, fillets and rounds may be employed at interfacing surfaces. For example, at least a proximal end of each of the Quonset-shaped wedges of the tip insert may be provided with rounded corners to facilitate insertion of the male projection at the distal end of the malleable cannula.

The three sub-assemblies of the device of the present disclosure, and the manner in which they engage and cooperate with one another, are explained in greater detail in the following detailed description of the preferred embodiments, with reference to the accompanying drawing figures.

BRIEF DESCRIPTION OF THE SEVERAL VIEWS OF THE DRAWING

FIG. 1 is a plan view of a conventional dual syringe and elongate applicator assembly;

FIG. 2 is an exploded view of a conventional elongate applicator assembly, including a luer hub sub-assembly having a proximal hub and a distal hub, an elongate, three-lumened cannula, and a spray tip sub-assembly including a round tip insert and a tip cap;

FIG. 2A is an enlarged exploded view of the region of FIG. 2 designated as "FIG. 2A", illustrating the spray tip sub-assembly of the conventional elongate applicator assembly of FIG. 2;

FIG. 3 is an exploded view of a mixing and dispensing device of the present disclosure, including a luer hub sub-assembly having a proximal hub and a distal hub, a malleable, four-lumened cannula, and a spray tip sub-assembly including a triangular tip insert and a tip cap;

FIG. 4 is an end view of the malleable cannula of the mixing and dispensing device of the present disclosure, taken along lines 4-4 of FIG. 3;

FIG. 5 is an exploded view of the luer hub sub-assembly of the mixing and dispensing device of the present disclosure;

FIG. 6 is a cross-sectional view, taken along lines 6-6 of FIG. 5, of the luer hub sub-assembly, with the proximal hub and distal hub of the luer hub sub-assembly engaged with one another, and illustrating in cross-section a proximal end of the malleable cannula received in a cannula-receiving opening of the distal hub of the luer hub sub-assembly, with each of the two fluid carrying lumens of the malleable cannula in fluid communication with a respective fluid path through the distal hub and proximal hub of the luer hub sub-assembly, through which the fluid carrying lumens of the malleable cannula may be placed in fluid communication with respective barrels of a dual syringe;

FIG. 7 is an exploded view of one embodiment of a spray tip sub-assembly of a mixing and dispensing device of the present disclosure;

FIG. 7A is an end view, taken along lines 7A-7A of FIG. 7, of the tip insert of FIG. 7;

FIG. 8 is an exploded view of an alternate embodiment of a spray tip sub-assembly of a mixing and dispensing device of the present disclosure;

FIG. 9 is an exploded view of the spray tip sub-assembly of the mixing and dispensing device illustrated in FIG. 3;

FIG. 10 is an exploded view of yet an additional embodiment of a spray tip sub-assembly of a mixing and dispensing device of the present disclosure similar to the spray tip sub-assembly of FIGS. 3 and 9, but with an alternate tip cap;

FIG. 10A is an enlarged plan view of the end wall of the tip cap, schematically illustrating the acceleration and mixing of two components in feeders or feeder channels and in a spinner region provided in the end wall;

FIG. 11 is an end view and partial cross-section view of the spray tip sub-assembly of FIG. 10;

FIG. 12 is a cross-sectional view, taken along lines 12-12 of FIG. 11, illustrating the tip insert of FIG. 10 engaged with the tip cap of FIG. 10, and further illustrating a distal end of a malleable cannula of the mixing and dispensing device of the present disclosure received in the tip cap and engaged with the tip insert, with alignment pins of the tip insert received in a wire-carrying lumen and in a vacant lumen of the malleable cannula;

FIG. 16 is an exploded perspective view of another alternate embodiment of a spray tip sub-assembly, with a broken away portion of a malleable cannula and an alternate distal end of a cannula;

FIG. 17 is an exploded rear view of a tip insert of a spray tip sub-assembly of FIG. 16, wherein the tip insert has a substantially octagonal shape;

FIG. 18 is a perspective view of the spray tip sub-assembly of FIG. 16, illustrating the tip insert within a tip cap of the spray tip sub-assembly and a mixed component being released from a delivery opening at a distal end of the tip cap, the mixed component illustrated by lines having both solid and hollow bubbles, the solid bubbles representing a first mixing component and the hollow bubbles representing a second mixing component;

FIG. 19 is a cross-sectional view of the spray tip sub-assembly taken along lines 19-19 of FIG. 18, illustrating the tip insert keeping first and second mixing components from mixing prematurely when fluid passes from the cannula and into the tip insert of the spray tip sub-assembly;

FIG. 20 is another cross-sectional view of the spray tip sub-assembly taken along lines 20-20 of FIG. 18, illustrating the angled indentations directing fluid from the fluid carrying channels of the cannula toward a space between the walls of the tip insert and the tip cap;

FIG. 21 is another cross-sectional view of the spray tip sub-assembly taken along lines 21-21 of FIG. 18, illustrating the fluid even further directed from the fluid carrying channels of the cannula into the tip insert and tip cap;

FIG. 22 is another cross-sectional view of the spray tip sub-assembly taken along lines 22-22 of FIG. 18, illustrating the fluid directed to feeders or feeder channels of the tip cap, some of which has been already mixed in one feeder or feeder channel, wherein other fluids will not be mixed until after the feeders or feeder channels deliver the fluids to the spinner region;

FIG. 33 is a top plan view of a proximal hub of a luer hub sub-assembly of the present disclosure;

FIG. 34 is a cross-sectional view of the proximal hub of FIG. 33 taken along the lines 34-4 of FIG. 33;

FIG. 35 is a perspective view of the distal hub of a luer hub sub-assembly of the present disclosure;

FIG. 36 is a top view of the distal hub of FIG. 35;

FIG. 37 is a cross-sectional view taken along lines 37-37 of FIG. 36;

FIG. 38 is an enlarged view of the region indicated by the circle designated "FIG. 38" in FIG. 37;

FIG. 39 is an enlarged view of the region indicated by the circle designated "FIG. 39" in FIG. 36; and FIG. 40 is a perspective view of a syringe assembly that may be used with each of the luer hub sub-assemblies and cannulae referenced herein.

DETAILED DESCRIPTION OF THE PREFERRED EMBODIMENTS

Figure 13:
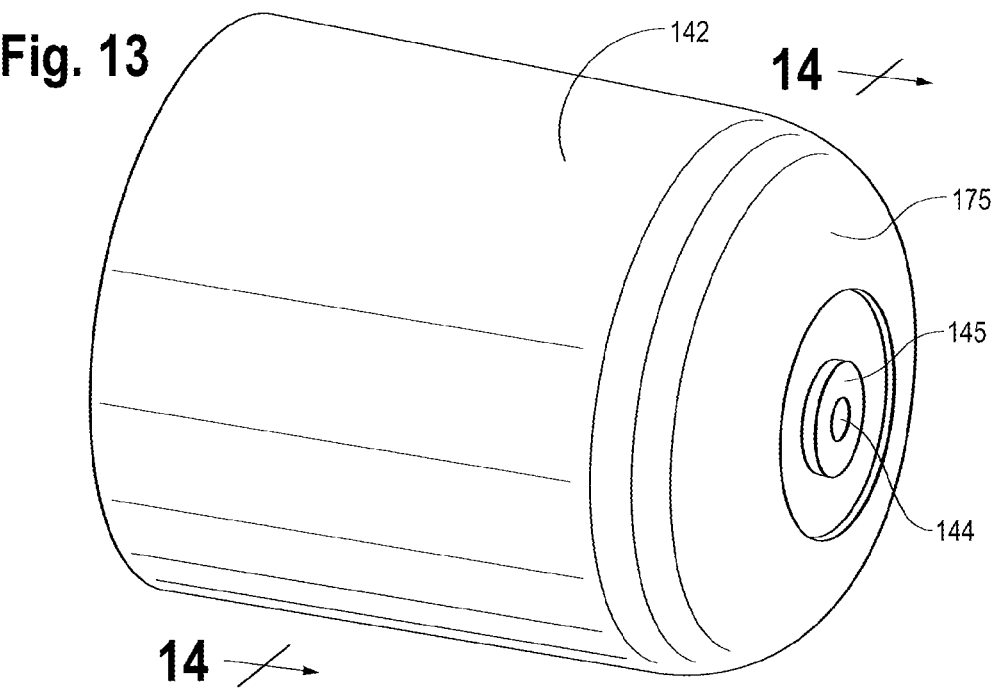
FIG. 13 is a perspective view of the exterior of the tip cap of the spray tip sub-assembly of FIG. 10.

As illustrated in FIGS. 1, 2 and 2A, a conventional kit 10 for mixing and applying a two-component surgical sealant to a tissue site includes a dual syringe 12, a luer hub sub-assembly 14, a cannula 16, and a spray tip sub-assembly 18. The luer hub sub-assembly includes a proximal hub 20 and a distal hub 22. The proximal hub 20 includes a pair of fluid channels 24, 26 placed into fluid communication with a respective one of the barrels of the dual syringe 12 when the luer hub sub-assembly 14 is docked with the dual syringe 12 via slip luer connections. The distal hub 22 also includes two distinct fluid channels (not shown in FIG. 2), which are in fluid communication with the respective fluid channels 24, 26 of the proximal hub 20. The fluid channels of the distal hub 22 converge toward one another, but remain physically separated, and are in further fluid communication with respective fluid-carrying lumens 30, 32 provided within the cannula 16. The cannula 16 also includes a third lumen 34.

As illustrated in FIG. 2A, the spray tip sub-assembly 18 includes a circular tip insert 28 having two alignment posts 36, 38 extending from a proximal side of the tip insert 28 that are received in the distal ends of the fluid-carrying lumens 30, 32. Each of the alignment posts 36, 38 includes at least one aperture therethrough to carry fluid from the respective lumens 30, 32 into radially extending grooves of 39, 41 of a recessed region 40 of the distal side of the tip insert 28, which abuts an interior surface of a tip cap 42. More specifically, fluid from lumen 30 is first directed into the radially extending groove 39 and fluid from lumen 32 is first directed into the radially extending groove 41. The fluids from each of lumens 30 and 32 are kept separate from each other as they enter the radially extending grooves 39, 41. After the fluid enters the radially extending grooves 39, 41, the fluid then enters a spinning chamber or center area of the recessed region 40 by a spinning motion. It is in this spinning chamber where fluid from lumen 30 first contacts fluid from lumen 32 before mixing. Thus, the recessed region 40 cooperates with the interior surface of the tip cap 42 to form a mixing chamber where the two fluids from the dual syringe 12, which initially came into contact with each other in the spinning chamber, are then mixed immediately prior to delivery through a delivery opening 44 provided in the tip cap 42.

Although the conventional surgical sealant mixing and application kit 10 is intended to be suitable for one-handed operation, due at least in part to the number of connections involved, medical professionals often resort to using both hands when operating the kit 10 to mix and apply tissue sealant. The following improvements address these and other drawbacks of the conventional tissue sealant kit 10.

Several embodiments of an improved device for mixing and applying a multi-component composition will now be described.

Referring now to FIG. 3, an applicator 100 of a first embodiment of the present disclosure is illustrated. The applicator 100 includes a luer hub sub-assembly 114, a cannula 116, and a spray tip sub-assembly 118. The luer hub sub-assembly 114 includes a proximal hub 120 and a distal hub 122, with the proximal hub 120 including fluid channels 124 and 126 to be placed in fluid communication with respective barrels of a dual syringe (not illustrated in FIG. 3). The distal hub 122 includes two distinct fluid channels 146, 148 (FIG. 5) in fluid communication with the respective fluid channels 124, 126 of the proximal hub 120.

The cannula 116 is preferably a malleable cannula extruded from a soft thermoplastic polyurethane elastomer, such as The Dow Chemical Company's Pellethane™ with four lumens, each of which is more closely illustrated in FIG. 4. Two of the lumens are fluid-carrying lumens 130, 132, each of which has a diameter preferably in the range of approximately 0.03"-0.06", and most preferably, approximately 0.046". A third lumen 134 may receive a wire 164 (illustrated in cross-section in FIG. 12), which is preferably an annealed wire. The soft thermoplastic polyurethane elastomer of the malleable cannula 116 and the annealed wire, in conjunction with one another, result in improved malleability, making the cannula 116 easier for medical personnel to bend the cannula 116 into a desired shape that is maintained after the cannula 116 is released. The diameter of the third lumen 134 is preferably in the range of approximately 0.03"-0.06", and most preferably, approximately 0.03", to accommodate an annealed wire 164 having a diameter of approximately 0.03". A fourth lumen 162 may remain vacant. Alternatively, the fourth lumen 162 could be employed to accommodate supplemental features such as, by way of example only, suction, pressurized gas, flushing solution, a light, a heat source, or a fiber optic camera. The fourth lumen 162 is considered desirable to include even if it remains vacant, as providing a fourth lumen 162 in the cannula 116 helps maintain substantially uniform wall thickness in the cannula 116 during extrusion thereof. The fourth lumen 162 may have a diameter greater than the diameter of each of the two fluid-carrying lumens 130, 132 and the third wire-carrying lumen 134. The diameter of the fourth lumen 162 is preferably in a range of approximately 0.03" to approximately 0.06", and most preferably, in a range of approximately 0.030" to approximately 0.050". The larger diameter of the fourth lumen 162 assists in distinguishing the respective lumens of the malleable cannula 116 to facilitate assembly of the applicator 100. The relatively large diameter of the fourth lumen 162 also helps to accommodate the optional supplemental features for which the fourth lumen 162 might be employed.

A proximal end region 154 of the malleable cannula 116 is received in a cylindrical female cannula-mating port 156 provided on a distal side of the distal hub 122. The proximal end region 154 of the malleable cannula 116 is provided with an elongate opening or slot 158 that receives a webbing 160 (FIG. 6) projecting from the distal side of the distal hub 122 within the cylindrical female cannula-mating port 156. As illustrated in FIG. 6, the webbing 160 may be aligned with a rib or wall 163 projecting on the proximal side of the distal hub 122 that separates the fluid channels 146, 148 of the distal hub 122. When received in the slot 158, the webbing 160 extends through the third and fourth lumens 134, 162 of the malleable cannula 116.

Referring now to FIGS. 5 and 6, each of the fluid-carrying lumens 130, 132 is placed into fluid communication with a respective fluid path hole 147, 149 of the fluid channels 146, 148 of the distal hub 122 of the luer hub sub-assembly 114. The fluid channels 146, 148 are each defined by a groove 146a, 148a (FIG. 6) in a proximal surface 150 of the distal hub 122 and by a distal surface 152 of the proximal hub 120. In a particularly preferred embodiment, each of the fluid channels 146, 148 of the distal hub 122 has a diameter of approximately 0.05". Each of the fluid path holes 147, 149 has a diameter in a range of approximately 0.02" to approximately 0.05", and most preferably, 0.046".

As illustrated in FIGS. 9-15, in certain embodiments of the present disclosure, the spray tip sub-assembly 118 of the applicator 100 includes a triangular tip insert 128. As illustrated in FIG. 9, the triangular tip insert 128 is received in a tip cap 142 having a delivery opening 144 through an end wall 175. The delivery opening 144 has a length in a range of approximately 0.01" to about 0.04", preferably about 0.02". The delivery opening 144 may be formed as a circular opening with an orifice diameter in a range of approximately 0.010 to 0.020". In order to achieve a fan-type spray, the delivery opening 144 may be provided with an oval-shaped slit 199, as illustrated in FIG. 12. Alternately, as illustrated in FIG. 13, a nipple 145 may be provided about the delivery opening 144. The nipple 145 promotes dispersion of spray. Alternately, as illustrated in FIG. 9, an elongate nipple region 145 may be provided on both sides of the delivery opening 144. The distal, exterior surface of the end wall 175 of the tip cap 142 may vary in topography, reminiscent to a mechanical break-up unit found in conventional commercial spray applicators. The varied topography helps overcome surface tension effects of the mixed fluid and aids in atomization.

Referring now to FIGS. 10 and 10A, the triangular tip insert 128 is preferably secured to the interior of the tip cap 142 by three guide pins 182, 184 and 186 provided on a proximal side of the end wall 175. The guide pins 182, 184, 186 mate with complementary pin-receiving holes 188, 190, 192 provided in a distal end of the triangular tip insert 128. The proximal side of the end wall 175 is provided with a plurality of feeders or feeder channels 194, 196, 198.

Referring, for example, to FIG. 11, the feeders or feeder channels 194, 196, 198 serve to deliver fluid from the three side walls 177a, 177b, 177c of the triangular tip insert 128 toward the recessed spinner region 180 so the fluids can be fully mixed with one another immediately prior to passing through the delivery opening 144 through the end wall 175. Thus, the fluids are mixed only after having been maintained in isolation from one another from the barrels of the dual syringe, through the luer hub sub-assembly 114, the malleable cannula 116, and into the spray tip sub-assembly 118, all of which will be explained in more detail below.

Figure 14:
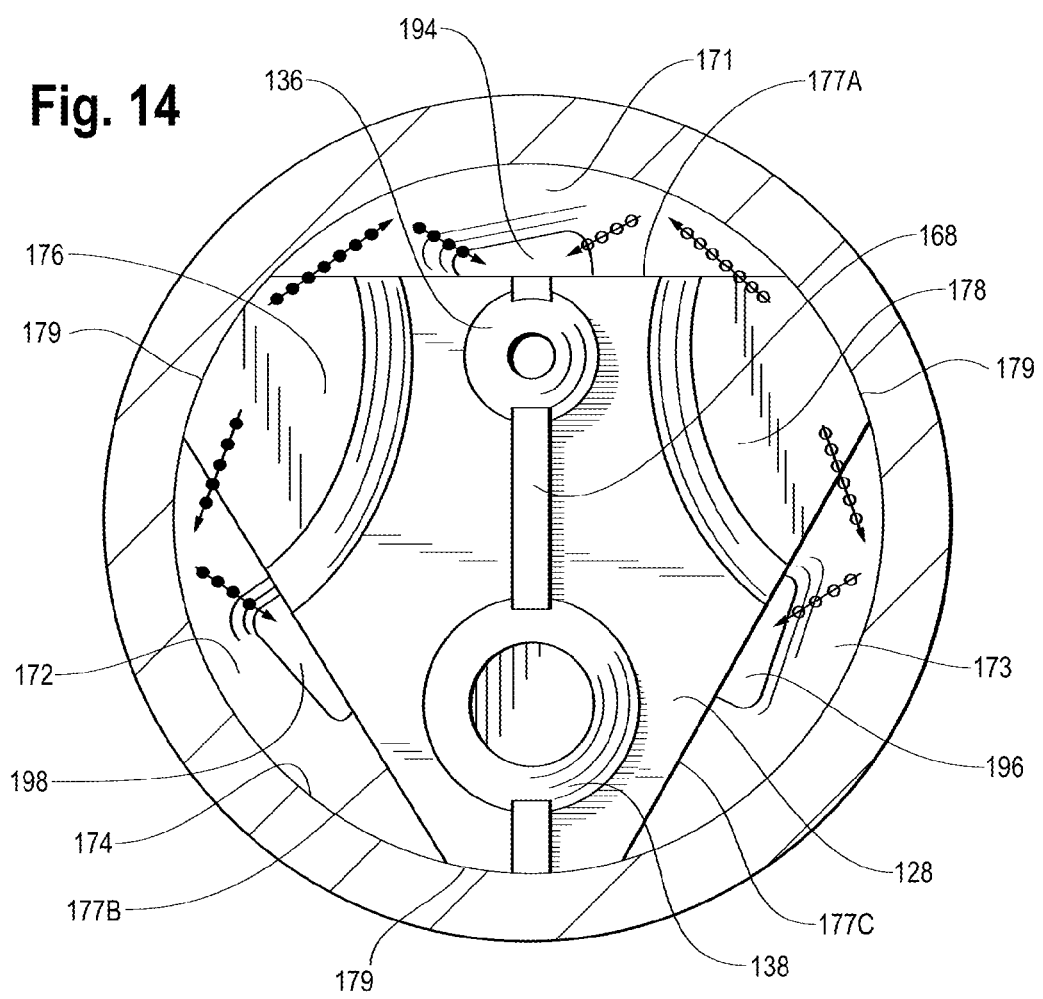
FIG. 14 is an enlarged cross-sectional view, taken along lines 14-14 of FIG. 13, of the spray tip sub-assembly of FIG. 10, with directional arrows illustrating the flow of fluid onto angled indentations of the tip insert, deflected beyond the sides of the tip insert, and toward a spinner region provided in an underside of the tip cap.

As illustrated in FIG. 14, the proximal side of the triangular tip insert 128 is provided with angled indentations 176, 178, with one of the angled indentations 176, 178 provided on either side of the alignment posts 136, 138 and the webbing 168. The angled indentations 176, 178 serve to redirect fluid flow from the two fluid-carrying lumens 130, 132 to openings in the form of arcuate segments 171, 172, 173 defined between each of the three side walls 177a, 177b, 177c of the triangular tip insert 128 and an inner surface 174 of the tip cap 142, and toward a recessed spinner region 180 embedded in the proximal side of the end wall 175 of the tip cap 142. The inner surface 174 may be the inner surface of the cylindrical wall of the tip cap 142.

As also illustrated in FIG. 14, rounded tips 179 (see also FIGS. 15 and 15A) of the triangular tip insert 128 contact the inner surface 174 of the tip cap 142, forming a seal between the interior surface 174 of the tip cap 142 and the triangular tip insert 128. This seal helps properly direct an accurate amount of fluid coming from each of the angled indentations 176, 178 into their respective arcuate segments 171, 172, and 173. The seal also prevents fluid from inadvertently going between the inner surface 174 of the tip cap 142 and angular sections of the triangular tip insert 128, preventing an improper amount of fluid from being directed to one of the arcuate segments 171, 172, 173 and resulting in an inadequate proportion of fluid components being mixed. In other words, the seals help ensure that an accurate amount of fluid from each fluid carrying lumens flows from the angled indentations into one or more of the arcuate segments 171, 172 and 173. If too much fluid from the angled indentations 176 and 179 inadvertently flows into any one of the arcuate segments 171, 172, and 173, the resulting mixture of components will be inadequate. The rounded tips form an interference seal to the tapered internal hole of the tip cap As indicated in FIGS. 14, 15 and 15A, a solid-bubbled line represents a first component exiting the first fluid-carrying lumen 130 of the malleable cannula 116 and a hollow-bubbled line represents a second component exiting the second fluid-carrying lumen 132 of the malleable cannula 116.

Notably, the angled indentation 176 deflects the first component through arcuate segment openings 171 and 172, and into feeders or feeder channels 194, 198, while angled indentation 178 deflects the second component through arcuate segment openings 171 and 173, and into feeders or feeder channels 194 and 196. Thus, mixing of the first and second component within the spray tip sub-assembly 118 is initiated gradually, as a desired portion of the first and second components are first exposed to one another in arcuate segment opening 171 and feeder or feeder channel 194. Fillets and rounds, such as rounded tips 179 of the triangular insert 128 contact the inner surface 174 of the tip cap 142 to help make sure the first and second components passing through arcuate segment openings 172 and 173, respectively, and entering feeders or feeder channels 196 and 198, are kept separate from one another. Even though only two mixing components exit the fluid carrying lumens 130, 132, a first component exiting the first fluid carrying lumen 130 and a second component exiting the second fluid carrying lumen 132, there are three streams of different fluids entering each of the feeders or feeder channels 194, 196, 198 prior to mixing. Specifically, because the angled indentation 176 deflects the first component through both arcuate segments 171 and 172 and angled indentation 178 deflects the second component through both arcuate segments 171 and 173, the first and second components first contact each other in the arcuate segment 171 before even entering the feeder or feeder channel 194, as illustrated in FIG. 14. By design, a combination of the first and second components then enters feeder or feeder channel 194 before mixing, only the first component enters feeder or feeder channel 198 before mixing, and only the second component enters feeder or feeder channel 196 before mixing. The first and second components are kept separate from each other in feeders or feeder channels 198 and 196 respectively, until all the fluid components from the separate feeders or feeder channels converge as they approach the center of the spinner region 180, causing a vortex that completes the mixing of the components immediately prior to delivery through the delivery opening 144.

The feeders or feeder channels 194, 196, 198 cooperate with the center of the spinner region 180 in such a manner as to enhance spinning so as to quickly and thoroughly mix the first, second components and mixture of components. As illustrated in FIGS. 10A and 15A, the triangular shape of each of the feeders or feeder channels 194, 196, 198 results in sidewalls that angle inward toward one another with increasing radial proximity within the passageway defined by the distal side of the triangular tip insert 128 and the feeder or feeder channel to the center of the spinner region 180. In other words, as the components in the feeders or feeder channels 194, 196, 198 approach the center of the spinner region 180, the cross-sectional area of the respective passageway defined by the distal side of the triangular tip insert 128 and the feeder or feeder channel decreases, causing an increase in velocity of the components, in a similar fashion to a converging nozzle. Thus, as the radial distance from the center of the spinner region 180 decreases, the cross-sectional area of the feeder or feeder channel decreases, causing an increase in velocity of the fluid components (represented schematically by arrows of increasing length), which reach a maximum velocity just prior to fluid entering the center of the spinner region 180, which serves as a mixing chamber. As the fluid components exit each of the feeders or feeder channels 194, 196, 198, they are propelled tangentially along the circular side wall 200 of the spinner region 180 to enforce the spinning, mixing action, forming a vortex, culminating in the spray of the mixed components through the delivery opening 144.

Figure 15:
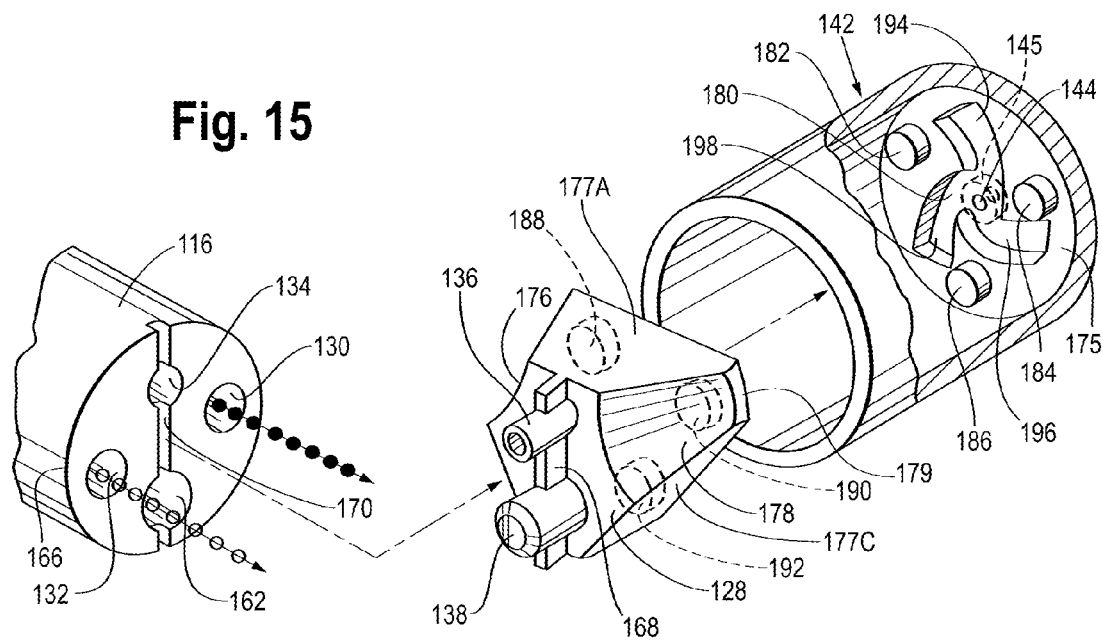
FIG. 15 is an exploded perspective view of the spray tip sub-assembly of FIGS. 10-14, with a broken-away portion of the malleable cannula and including a solid-bubbled line representing a first component exiting a first fluid-carrying lumen of the malleable cannula and a hollow-bubbled line representing a second component exiting a second fluid-carrying lumen of the malleable cannula.
Figure 15A:
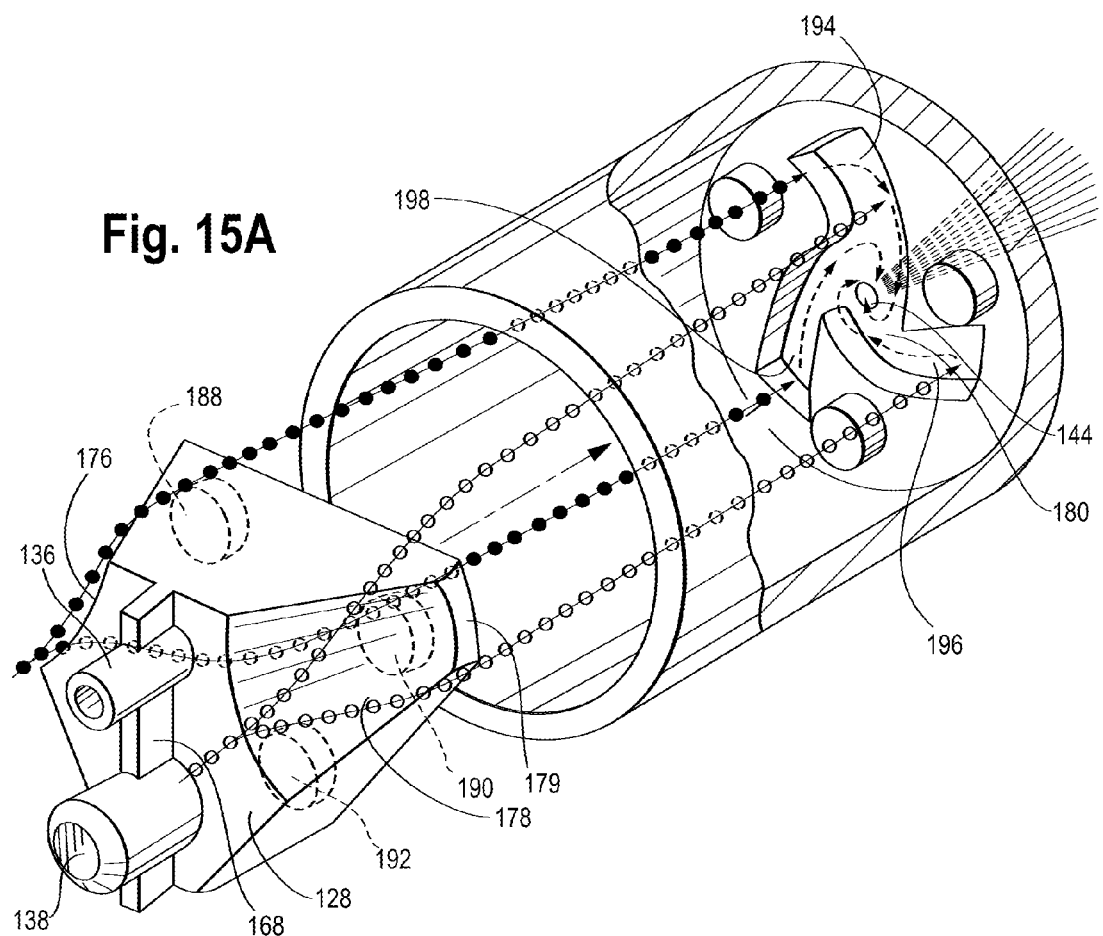
FIG. 15A is an exploded perspective view of the spray tip sub-assembly of FIG. 15, with a portion of the tip cap cut away, and with the solid-bubbled lines representing flow paths of the first component, and the hollow-bubbled lines representing flow paths of the second component, around sides of the tip insert and into the spinner region provided in the underside of the tip cap.

As illustrated in FIG. 15, the tip insert 128 includes a pair of alignment posts 136, 138 projecting from a proximal side thereof, the alignment posts 136, 138 received in the third and fourth lumens, 134, 162, respectively, at a distal end 166 of the malleable cannula 116. The alignment post 138 preferably has a larger diameter than the alignment post 136, to accommodate and monogamously mate with the corresponding fourth lumen 162 and third lumen 134, respectively. One or both of the alignment posts 136, 138 may be provided with a hollow portion, as illustrated in cross-section in FIG. 12, in order to accommodate, for example, a distal end portion of the annealed wire 164. If the fourth lumen 162 were to accommodate a device or fluid to be delivered or suctioned through, or otherwise exposed to, the delivery opening 144, then the alignment post 138 could be hollow.

A webbing 168 extends laterally between the alignment posts 136, 138 and continues beyond each of the alignment posts 136, 138. The webbing 168 of the tip insert 128 is received in an elongate opening or slot 170 in the distal end 166 of the malleable cannula 116, in a similar fashion to the manner in which the webbing 160 (FIG. 6) projecting from the distal end of the distal hub of the luer hub sub-assembly is received in the slot 158 in the proximal end region 158 of the cannula 116. The webbing 168 helps isolate fluid components flowing through each of the fluid-carrying lumens 130, 132 from one another as the fluid components pass from the malleable cannula 116, across the interface between the cannula 116 and the tip insert 128. In a preferred embodiment, the slots 158, 170 have a width of approximately 0.01", most preferably 0.012" and a depth of approximately 0.05", most preferably 0.049", and may be formed by cutting the proximal and distal ends of the extruded malleable cannula 116 with a blade or utilizing forming (tipping) methods known in the catheter industry.

A solvent is preferably applied to each of the slots 158, 170 to help prevent cross-talk between the fluids passing from the fluid channels 146, 148 of the distal hub 122 of the luer hub sub-assembly 114 to the fluid-carrying lumens 130, 132 of the malleable cannula 116, in the case of slot 158, and from the fluid-carrying lumens 130, 132 malleable cannula 116 to the apertures 172, 174 through the triangular tip insert 128, in the case of slot 170. In place of solvent an adhesive bonding (self-curing, uv-curing or thermal curing) may be used.

As illustrated in FIGS. 7, 7A, and 8, the spray tip sub-assembly may take alternate forms, such as having a substantially rectangular tip insert 248 with opposing flat side walls 277*a*, 277*b*, and opposing rounded side walls 277*c*, 277*d*. In the spray tip sub-assembly 218 illustrated in FIGS. 7 and 7*a*, the distal end of the substantially rectangular tip insert 248 (as opposed to the proximal surface of the end wall 275 of the tip cap 242) is provided with a recessed spinner region 280. Like the triangular tip insert 128, the substantially rectangular tip insert 248 is provided with angled indentations 276, 278 to direct fluid from the fluid-carrying channels of a cannula toward space between the flat side walls 277*a*, 277*b* and the interior surface of the cylindrical wall 273 of the tip cap 242. The substantially rectangular tip insert 248 may include alignment posts 236, 238, connected by a webbing 268, as best illustrated in FIG. 7A. The substantially rectangular tip insert 248 of the embodiment illustrated in FIG. 7 further includes feeders or feeder channels 294, 296 in the form of slots provided in the distal side of the tip insert 248. A petal-shaped recessed region 281 of the interior of the end wall 275 of the tip cap 242 extending from the delivery opening 244 cooperates with the recessed spinner region 280 to further facilitate mixing.

The spray tip sub-assembly 218A of the embodiment illustrated in FIG. 8 differs from the spray tip sub-assembly 218 illustrated in FIG. 7, in that the distal end of the substantially rectangular tip insert 248A has no recessed spinner region or feeders or feeder channels therein. Rather, the proximal surface of the end wall 275A of the tip cap 242A includes a recessed spinner region 280A, with feeders or feeder channels 294A, 296A, 298A leading thereto, to direct fluid into the spinner region 280A for mixing immediately prior to delivery through the delivery opening 244A.

Now referring to FIGS. 16-22, another alternate embodiment of a spray tip sub-assembly 318 is illustrated. More specifically, FIG. 16 illustrates an exploded perspective view of the spray tip sub-assembly 318 of FIG. 16, with a broken-away portion of a malleable cannula 316. The spray tip sub-assembly 318 of this embodiment includes a tip insert 348 having a substantially octagonal distal portion, with three substantially flat side walls 377a, 377b, and 377c, and five concave or rounded side walls 377d, 377e, 377f, 377g, 377h. A tip cap 342 of the spray tip sub-assembly 318 includes a cylindrical wall 373 and an end wall 375.

Like the malleable cannula 116 of FIG. 3, the malleable cannula 316 includes four lumens and is preferably a malleable cannula 316 extruded from a soft thermoplastic polyurethane elastomer, such as The Dow Chemical Company's Pellethane™. Two of the lumens are fluid carrying lumens 330, 332, each of which may also be placed into fluid communication with the respective fluid path hole 147, 149 (see FIG. 6) of the fluid channels 146, 148 of the distal hub 122 of the luer hub sub-assembly 114. The malleable cannula 316 also includes a third lumen 334, which may receive a wire resulting in improved malleability of the cannula 316, and a fourth lumen 362, which may be employed to accommodate, for example, suction, pressurized gas, flushing solution, a light, a heat source, or a fiber optic camera.

As illustrated in FIG. 16, a distal end region 366 of the malleable cannula 316 includes a pair of elongate notches where portions of the malleable cannula 316 are shaved or otherwise cut back to expose semi-cylindrical channel regions 330a and 332a, each of which is an extension of a respective one of the fluid carrying lumens 330, 332. The notches each extend axially along the malleable cannula 316, from a distal end wall 400 of the malleable cannula 316 to a stop wall 402 spaced axially inwardly (i.e., proximally) of the distal end wall 400. The semi-cylindrical channel regions 330a, 332a are each bounded along their lateral edges by alignment ledges 404, 406, 408, 410 (also illustrated in FIGS. 19 and 20) extending to the outer perimeter of the malleable cannula 316. The third and fourth lumens 334, 362 run between the alignment ledges 404, 408, and 406, 410, with the remaining portion of the malleable cannula 316 that surrounds the third and fourth lumens 334, 362 along the notches, and defining the semi-cylindrical channel regions, forming a male projection 370 of the malleable cannula 316. The male projection 370 is received in a female mating port 379 (as illustrated in FIG. 17) of the tip insert 348.

Like the triangular tip insert 128, the tip insert 348 includes structural features to direct fluid from the fluid carrying lumens 330, 332 of the malleable cannula 316 toward space between the tip insert 348 and the tip cap 342 when the tip insert 348 is secured to the distal end section 366 of the malleable cannula 316. As indicated in FIG. 17, these structural features include a pair of fluid path archways 381, 383, each of which align with a portion of a respective one of the semi-cylindrical channel regions 330a, 332a (FIG. 16) of the cannula 316.

Figure 26:
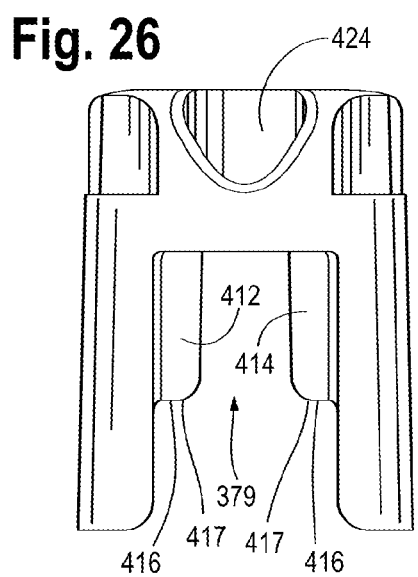
FIG. 26 is a front plan view of a tip insert of the spray tip sub-assembly of the embodiment illustrated in FIG. 16.
Figure 27:
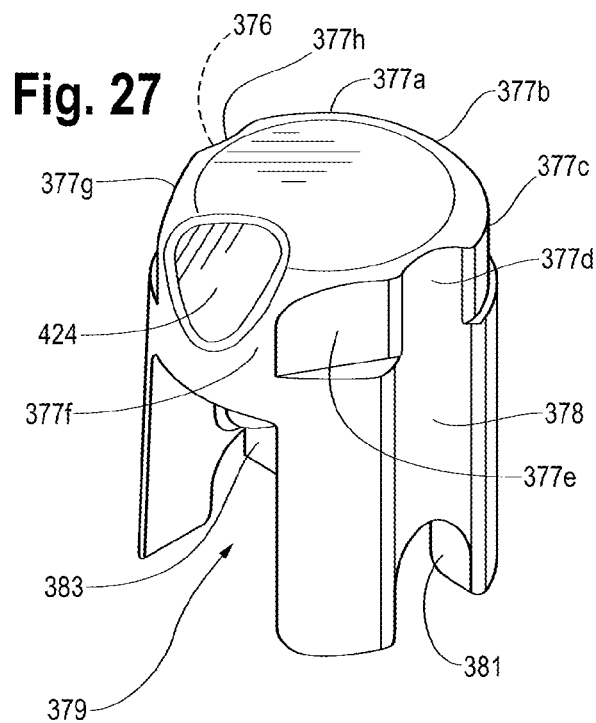
FIG. 27 is a perspective view of the tip insert of FIG. 26.
Figure 28:
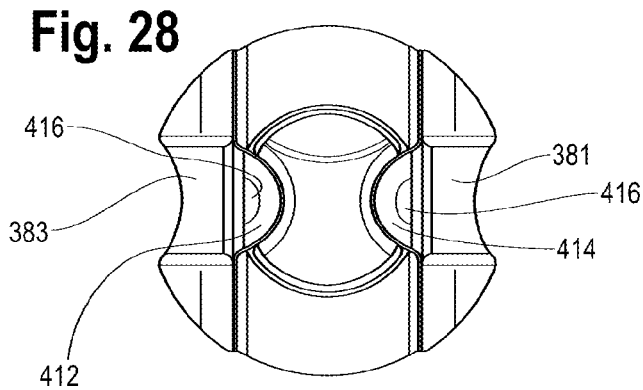
FIG. 28 is a bottom plan view of the tip insert of FIG. 26.

FIGS. 26-29 illustrate the additional structural features of the tip insert 348. For example, the tip insert 348 also includes a pair of substantially Quonset-shaped wedges 412, 414, both of which are illustrated in FIG. 26, that are axially aligned with a respective one of the fluid path archways 381, 383. As further illustrated in FIG. 26, each substantially Quonset-shaped wedge 412, 414 has a proximal surface 416 that includes fillets 417 or curved or rounded edges. When the male projection 370 of the malleable cannula 316 is engaged with the tip insert 348, each of these substantially Quonset-shaped wedges 412, 414 occupies a portion of a respective one of the semi-cylindrical channel regions 330a, 332a closer to the end wall 375 of the tip cap 342. While in this position, the fillets 417 of the proximal surfaces 416 of the Quonset-shaped wedges 412, 414 divert fluid from the fluid-carrying lumens through the fluid path archways 381, 383, into flow paths defined between crescent-shaped channels 376, 378 (FIG. 29) running axially along an exterior of the tip insert 348, and an inner surface 373a of the cylindrical wall 373 of the tip cap 342. The fillets 417 of the proximal surfaces 416 further help direct the male projection 370 of the malleable cannula 316 into engagement with the female mating port 379 of the tip insert 348 during assembly. Specifically, the concave or rounded corners of the fillets 417 enable the male projection 370 of the cannula 316 to easily glide into the female mating port 379 of the tip insert without getting caught on any angular edges or surfaces of the Quonset-wedges 412, 414, for example. By facilitating registration for assembly, the fillets 417 of the proximal surfaces 416 of the wedges 412, 414 allow a user to easily assemble the cannula 316 and the tip insert.

Figure 29:
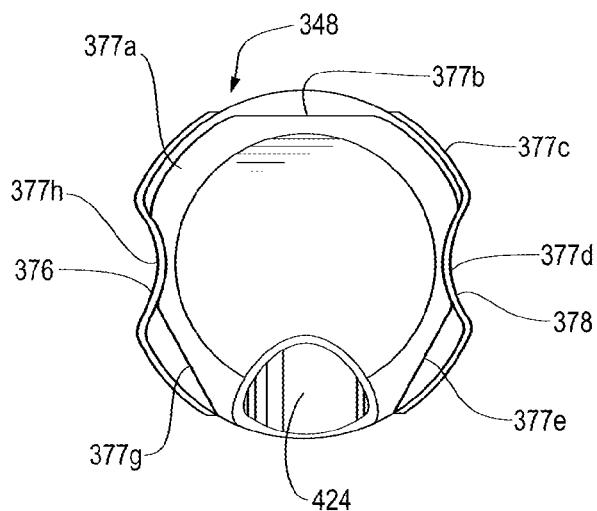
FIG. 29 is a top plan view of the tip insert of FIG. 26.
Figure 30:
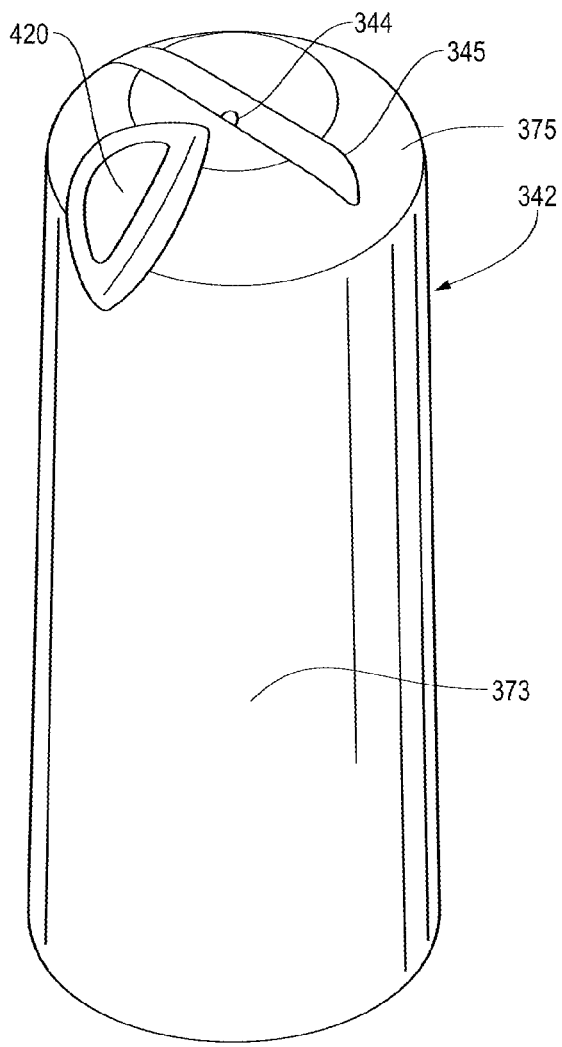
FIG. 30 is a perspective view of a tip cap of the spray tip sub-assembly of the embodiment illustrated in FIG. 16.
Figure 32:
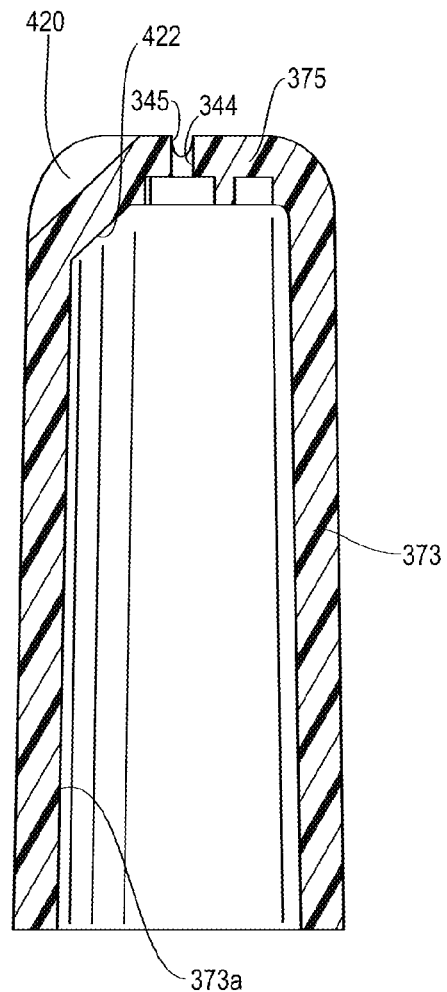
FIG. 32 is a cross-sectional view, taken along lines 32-32 of FIG. 31, of the tip cap of FIG. 30.
Figure 31:
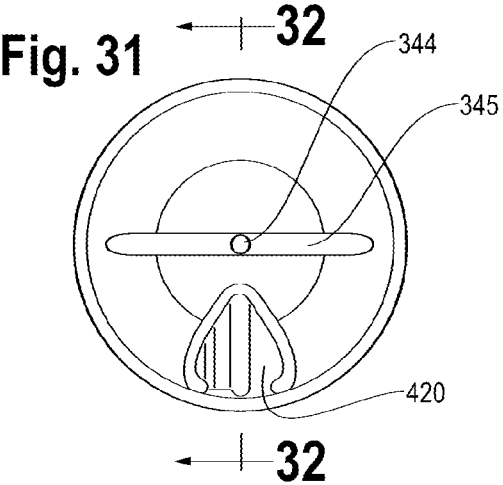
FIG. 31 is a top plan view of the tip cap of FIG. 30.

As illustrated in FIGS. 30, 31, and 32, the tip cap 342 may be provided with an inwardly-directed registration dimple or depression 420 in a region of the tip cap 342 where the cylindrical wall 373 of the tip cap 342 meets the end wall 375 of the tip cap 342. As further illustrated in FIG. 32, a corresponding interior region of the tip cap 342 has an inwardly-directed registration key 422. A complementary alignment keyway notch 424 (see FIGS. 26, 27 and 29) is provided in a distal end of the tip insert 348, which receives the inwardly-directed registration key 422 when the tip insert 348 is received in the tip cap 342. Engagement of the inwardly-directed registration key 422 of the tip cap 342 with the alignment notch 424 of the tip insert 348 assures proper alignment between the tip cap 342 and the tip insert 348.

As described in more detail below, FIGS. 19-21 illustrate a series of cross-sections through the spray tip sub-assembly 318, beginning with FIG. 19 at interface between the male projection 370 of the malleable cannula 316 and the spray tip sub-assembly 318, and continuing distally until a location immediately proximate the end wall 375 of the tip cap 342. Fluid components from each of the fluid carrying lumens 330, 332 flow into the respective semi-cylindrical channels 330a, 332a, contact the proximal surface 416 and fillet 417 of the Quonset-shaped wedges 412, 414, and are directed radially outwardly through the fluid path archways 381, 383 (i.e., in a direction radially opposite the fluid component from the other fluid carrying lumen 332, 330, which helps to prevent premature cross-talk between the fluid components in the two fluid carrying lumens 330, 332). The fluid components then flow distally, toward the spaces between the flat side walls 377a, 377b, and 377c and the rounded side walls 377d, 377e, 377g, and 377h of the substantially octagonal distal portion of the tip insert 348 and the interior surface 373a of the cylindrical wall 373 of the tip cap 342.

As further illustrated in FIG. 16, the tip cap 342 includes a spinner region 380 with feeders or feeder channels 394, 396, and 398 leading thereto. As in the previous embodiment, the feeders or feeder channels 394, 396, 398 are generally triangular in shape, with sidewalls that taper inwardly toward one another as they approach the center of the spinner region 380. The diminishing cross-sectional area of the feeders or feeder channels 394, 396, 398 as they approach the spinner region 380 causes an increase in the velocity of the fluid components, as in a converging nozzle. As the fluid components enter the spinner region 380 from the three feeders or feeder channels 394, 396, 398, a vortex effect is created, serving to mix the fluid flows immediately prior to spraying the mixed components through a delivery opening 344 of the tip cap 342.

FIG. 18 is a perspective view of the tip insert 348 within the tip cap 342 of the spray tip sub-assembly 318. A mixed component is being released from the delivery opening 344 at a distal end of the tip cap 342. The mixed component is shown by an alternating pattern of solid-bubbled and hollow-bubbled lines, wherein the solid bubbles represent a first component and the hollow bubbles represent a second component. Thus, the component is already mixed together before it is released from the delivery opening 344. The tip cap 342 is also provided with an elongate nipple region 345 on a distal side of the end wall 375 of the tip cap 342, intersecting the delivery opening 344. This elongate nipple region 345 serves to cause the tissue sealant formed of the mixed fluid components to disperse in a fan-like pattern, thereby promoting spraying of a desired tissue surface. As illustrated in FIG. 3, the tip cap 142 of that embodiment may likewise be provided with such an elongate nipple region 145.

FIG. 19 is a cross-sectional view of the spray tip sub-assembly taken along the lines 19-19 of FIG. 18. The view shows the male projection 370 of the cannula 316 and the crescent-shaped channels 376 and 378 of the tip insert 348. The crescent-shaped channels 376 and 378 each carry only one mixing component from the fluid carrying lumens 330, 332. Specifically, the crescent-shaped channel 376 of the tip insert 348 is filled with solid bubbles representing a first mixing component, and the crescent-shaped channel 378 of the tip insert 348 is filled with hollow bubbles representing a second mixing component. At this point, the crescent-shaped channels 376, 378 of the tip insert 348 help keep the first and second mixing components from prematurely mixing when fluid passes from the malleable cannula 316 and into the tip insert 348 of the spray tip sub-assembly 318.

FIG. 20 is a cross-sectional view of the spray tip sub-assembly 318 taken along the lines 20-20 of FIG. 18. Here, the crescent-shaped channels 376, 378 of the tip insert 348 have directed the fluid from the fluid carrying channels 330, 332 of the malleable cannula 316 toward a space between walls of the tip insert 348 and the tip cap 342. The two mixing components are still separate from each other.

FIG. 21 is a cross-sectional view of a spray tip sub-assembly 318 taken along the lines 21-21 of FIG. 18. As illustrated in this view, the fluid has been even further directed from the fluid carrying channels 330, 332 of the malleable cannula 316 into the tip insert 348 and the tip cap 342. The first mixing component, indicated by solid bubbles, is now found in the space or first flow path A formed between the substantially flat side walls 377a, 377b and the rounded side walls 377g, 377h of the tip insert 348 and the interior surface 373a of the cylindrical wall 373 of the tip cap 342. The second mixing component is represented by hollow bubbles and is found in the space or second flow path B formed between the substantially flat side walls 377b, 377c and rounded side walls 377d, 377e of the tip insert 348 and the interior surface 373a of the cylindrical wall 373 of the tip cap 342. A portion of the solid-bubbled mixing component is about to mix with the hollow-bubbled mixing component in an area or third flow path C between the substantially flat side wall 377b of the tip insert 348 and the interior surface 373a of the tip cap 342.

As illustrated in FIGS. 21 and 29, for example, like the rounded tips 179 of the triangular tip insert 128, the octagonal tip insert 328 includes rounded areas 377a and 377c extending from each side of substantially flat side wall 377b to rounded side walls 377d and 377h, respectively. These rounded areas of the octagonal tip insert 328 are spaced from the inner surface 373a of the tip cap 34, forming annular transfer channels 350, 352 between the interior surface of the tip cap 342 and the octagonal tip insert 328 and ensuring a correct proportion or portion of each fluid component is being properly directed into the third flow path C formed between the flattened wall 377b and the tip cap 342. More specifically, a first transfer channel 350 is formed between the first flow path A and the third flow path C, and a second transfer channel 352 is formed between the second flow path B and the third flow path C. These transfer channels 350, 352 between the tip insert 348 and the tip cap 342 are designed such that a desired portion of each of the first and second mixing components may be forced together in the third fluid flow path C, thereby forming a mixture of the first and second mixing components before entry into the feeder or feeder channel 394. See, e.g., FIGS. 21 and 22.

More specifically, the configuration of the tip insert 348 and the tip cap 342 is such that three flow paths for three fluid streams are created before each of the fluid streams enters one of the three feeders or feeder channels 394, 396, and 398 disposed in the tip cap 342. The interference fit between the tip insert 346 and tip cap 342 prevents cross talk between the feeder channels 394, 396, and 398. A ratio of the portions of the components being mixed can be set by dimensioning an interface and spacing of the transfer channels 350, 352 between the tip insert 348 and the tip cap 342, such that a desired proportion of the first mixing component only becomes one fluid stream, a desired proportion of the second mixing component only becomes a second fluid stream, and a desired proportion of the remaining portions of both the first and second mixing components become a third fluid stream, each of the fluid streams being created before separately entering the three feeders or feeder channels 394, 396, and 398. By maintaining the isolation of portions of the first and second mixing components and premixing the remaining portions of the first and second mixing components before any component enters the feeders or feeder channels 394, 396 and 398, mixing is optimized without leading to increased clogging.

FIG. 22 illustrates another cross-sectional view of a spray tip sub-assembly 318 this time taken along the lines 22-22 of FIG. 18. Here, the fluid has been directed to feeders or feeder channels 394, 396, and 398. The feeder 394 includes fluid components that have already begun to mix with one another, as illustrated by a combination of both the solid- and hollow-bubbled mixing components in that feeder 394. The feeder 396 includes the hollow-bubbled (second) mixing component only, and the feeder 398 includes the solid-bubbled (first) mixing component only. Thus, the two fluid components have already begun to mix with one another before the feeder 394 delivers the fluid to the spinner region 380; however, the other feeders or feeder channels 396 and 398 respectively deliver first and second mixing components that have not started mixing with one another. Instead, the first mixing component included in feeder 398 and the second mixing component included in feeder 396 are not mixed until the feeders or feeder channels 396, 398 deliver the respective components to the spinner region 380, at a relatively high velocity, wherein they are mixed in a vortex. This configuration allows the fluid components to gradually begin mixing with one another, since only that portion of each of the fluid components flowing into the feeder 394 begins mixing with the other fluid component prior to entry into the spinner region 380. The remaining portions of the fluid components flowing into one or the other of the feeders or feeder channels 396, 398 remain isolated from the other fluid component until reaching the spinner region 380. Thus, the remaining portions of the fluid components are mixed only immediately before passing through the delivery opening 344 of the tip cap 342 and have been maintained in isolation from one another from the barrels of the dual syringe 12, through the luer hub assembly 114 and the malleable cannula 316, and into the spray tip sub-assembly 318.

Figure 23:
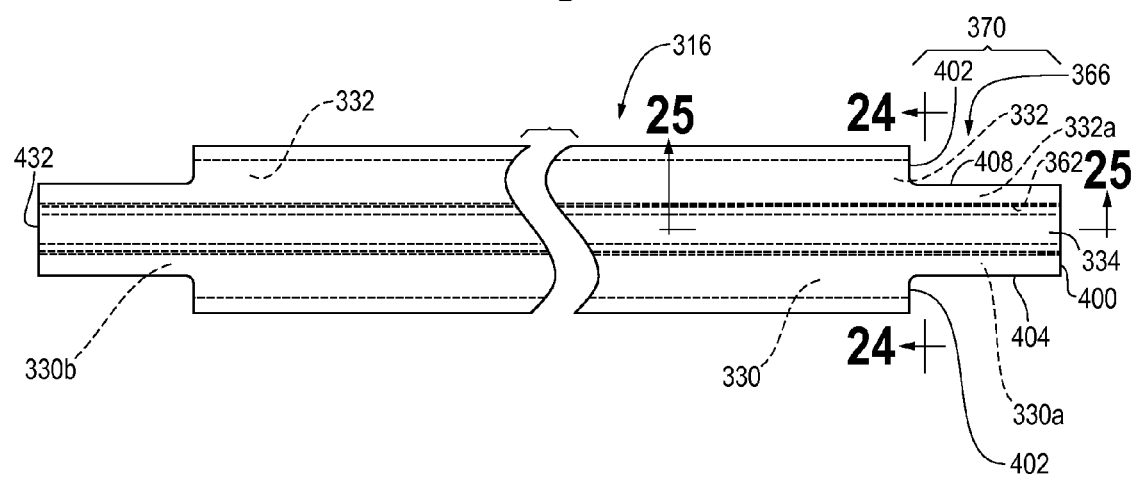
FIG. 23 is a plan view of the cannula of FIG. 16.

Referring now to FIG. 23, the malleable cannula 316 further includes a proximal end region 354 having two elongate notches where portions of the malleable cannula 316 are shaved or otherwise cut back to expose semi-cylindrical channel regions, each of which is an extension of a respective one of the fluid carrying lumens 330, 332. Like the male projection 370 at the distal end region 366, a male projection 430 is defined at the proximal end region 354 by that area of the malleable cannula 316 between the two elongate notches. The notches at the proximal end region 354 extend axially along the malleable cannula from a proximal end wall 432 of the malleable cannula 316 to a stop wall 434 spaced axially inwardly (i.e., distally) of the proximal end wall 432.

The male projection 358 may engage a complementary female cannula mating port (not shown) of the distal hub of a luer sub-assembly, in a manner that directs the fluid components into the respective fluid carrying lumens 330, 332, without cross-talk between the fluid components.

Figure 24:
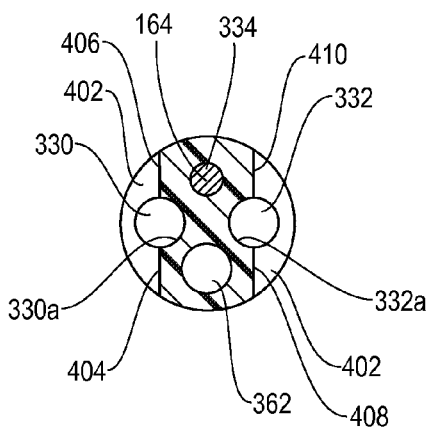
FIG. 24 is a cross-sectional view of the cannula taken along the lines 24-24 of FIG. 23.

FIG. 24 is a cross-sectional view of the malleable cannula 316 taken along the lines 24-24 of FIG. 23. The view illustrates all four lumens of the malleable cannula 316, the two fluid carrying lumens 330, 332, the third lumen 334, which may receive an annealed wire 164, and the fourth lumen 362.

Figure 25:
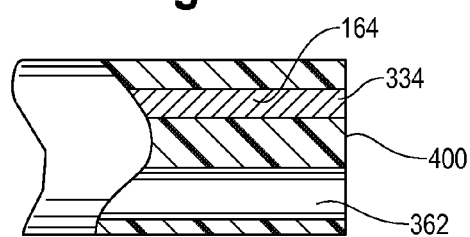
FIG. 25 is a cross-sectional view of the cannula taken along the lines 25-25 of FIG. 23.

FIG. 25 is a cross-sectional view of the malleable cannula 316 taken along the lines 25-25 of FIG. 23. The view illustrates the third and fourth lumens 334, 362, wherein the third lumen 334 may accommodate an annealed wire 164, helping to preserve a desired shape of the malleable cannula 316.

FIGS. 33 and 34 illustrate a proximal hub 320 of a luer hub sub-assembly 114 that may be used with the distal hub 122 and any of the malleable cannulae 116, 316 referred to herein. A top plan view of the proximal hub 320 is illustrated in FIG. 33, and a cross-sectional view of the proximal hub 320 taken along the lines 34-34 of FIG. 33 is illustrated in FIG. 34. Like the proximal hub 120 of FIG. 5, the proximal hub 320 includes two fluid channels 324, 326 to be placed in fluid communication with respective barrels 510, 512 of a dual syringe. The barrels 510, 512 form reservoirs of the first component and the second component. The fluid channels 146, 148 (FIG. 5) of the distal hub 122 may alternatively be placed in fluid communication with the respective fluid channels 324, 326 of the proximal hub 320. A blade 325, as illustrated in FIG. 34, extends rearward adjacent to fluid channel 324 and fits into a slot 502 of a syringe assembly 500, as indicated in FIG. 40, to securely anchor the proximal hub 320 to the syringe assembly 500. Fitting the blade 325 into the slot 502 enables a surgeon to move the syringe assembly 500 around without leading to a disconnection of the syringe assembly 500 and the proximal hub 320 during use. The engagement is further strengthened by tabs 327 extending out sides adjacent to each of the fluid channels 324, 326 of the proximal hub 320, as shown in FIGS. 33 and 34, and actuable clips 504 shown on either side of the syringe assembly 500 of FIG. 40. More specifically, after the blade 325 is inserted into the slot 502 of the syringe assembly, the clips 504 on either side of the syringe assembly are placed on the tabs 327 of the proximal hub 320, thereby resulting in a reinforced, secure connection between the proximal hub 320 and the syringe assembly 500.

As illustrated in FIG. 40, the syringe assembly may include two push tabs 506 connected to and below each of the clips 504 to enable movement of the clips to an open position that allow the proximal hub 320 and the blade 325 to be easily inserted within the syringe assembly 500. More specifically, to insert the blade 325 into the slot 502 of the syringe assembly 500, a user may first place her thumb and forefinger on each of the push tabs 506 connected to the clips 504, thereby placing the clips 504 in an open position. With her other hand, the user may insert the blade 325 of the proximal hub 320 into the slot 502, and further insert the fluid channels 324, 326 into the fluid containing barrels of the syringe assembly 500. The user may then release her thumb and forefinger from the tabs 506 attached to the clips 504 of the syringe, resulting in the clips 504 being easily placed on the tabs 327 of the proximal hub 320 and securely fastening the proximal hub 320 to the syringe assembly 500.

FIGS. 35-39 illustrate a distal hub of a luer-hub subassembly 322 intended to interface with the male projection at the proximal end of malleable cannula 316. As best illustrated in FIGS. 37 and 38, a projection-receiving channel is provided at the proximal end of the female cannula mating port of the distal hub. Fluid from each the channels within the luer-hub subassembly is diverted into a respective one of the semi-cylindrical channel regions along the male projection of the malleable cannula 316, facilitated by complementary wedges 321, 323 within the cylindrical female cannula mating port of the distal hub.

While the applicator of the present disclosure has been described with respect to certain embodiments thereof, it will be understood that variations may be made thereto that are still within the scope of the appended claims.

What is claimed is:

1. An apparatus for delivering a mixture of at least first and second fluid components contained in at least two respective reservoirs in a manner that prevents premature cross-contamination of the fluid components, comprising:

a luer hub sub-assembly configured to engage the at least two reservoirs and forming a first hub fluid channel and a second hub fluid channel to provide passage to a first fluid component and a second fluid component;

a malleable cannula including first and second fluid-carrying lumens, each of the first and second fluid-carrying lumens being in fluid communication with a respective one of the first hub fluid channel and second hub fluid channel; and a spray tip sub-assembly disposed at an end of the cannula including at least a portion of a tip insert received in a tip cap, the tip cap having an end wall with a delivery opening therethrough, the tip insert and the tip cap forming at least three feeder channels including a first feeder channel, a second feeder channel, and a third feeder channel, and the tip insert and the tip cap defining at least three flow paths in correspondence to the at least three feeder channels, each of the feeder channels being in fluid communication with a respective one of the flow paths, the tip insert and the tip cap forming fluid communication between the first fluid carrying lumen and a first flow path of the at least three flow paths to provide for passage of the first fluid component and fluid communication between a second flow path of the at least three flow paths to provide passage for the second component, a portion of the tip cap engaging the tip insert, the tip cap and the tip insert configured so that the engagement physically separates the first flow path from the second flow path, the tip insert and the tip cap forming a third flow path of the at least three flow paths, the tip cap and the tip insert forming a first transfer channel between the first flow path and the third flow path and a second transfer channel between the second flow path and the third flow path, wherein a portion of the first fluid component is permitted to flow through the first flow path into the first feeder channel, a portion of the second fluid component is permitted to flow through the second flow path into the second feeder channel, and the remaining portions of the first and second fluid components are permitted to flow through the first and second transfer channels into the third flow path and then into the third feeder channel, each of the first, second, and third flow paths being in the form of an arcuate segment defined between a side wall of the tip insert and an interior surface of the tip cap, through which fluid components from the first and second fluid-carrying lumens pass prior to entering the feeder channels, a first of the arcuate segments receiving a fluid component from only the first fluid-carrying lumen of the malleable cannula; a second of the arcuate segments receiving a fluid component from only the second of the fluid-carrying lumen of the malleable cannula; and a third of the arcuate segments receiving fluid components from the first and second flow paths via the first and second transfer channels.

2. The apparatus of claim 1, wherein the tip insert includes a plurality of angled indentations in a proximal side thereof.

3. The apparatus of claim 2, wherein a proximal side of the end wall of the tip cap includes a recessed spinner region therein and the plurality of feeder channels that direct fluid from the sides of the tip insert and into the recessed spinner region.

4. The apparatus of claim 1, wherein a proximal side of the end wall of the tip cap includes a recessed spinner region therein and the plurality of feeder channels that direct fluid from the sides of the tip insert and into the recessed spinner region.

5. The apparatus of claim 4, wherein each of the feeder channels is of a generally triangular shape, with two sidewalls that angle inward toward one another with increasing radial proximity to a center of the recessed spinner region.

6. The apparatus of claim 3, each of the at least two reservoirs having a fluid component therein, the fluid component from one of the reservoirs disposed in the first fluid-carrying lumen of the malleable cannula and the fluid component from another of the reservoirs disposed in the second fluid-carrying lumen of the malleable cannula, wherein:
  the first feeder channel receives a fluid component from only the first fluid-carrying lumen of the malleable cannula;
  the second feeder channel receives a fluid component from only the second fluid-carrying lumen of the malleable cannula; and
  the third feeder channel receives fluid components from both the first and second fluid-carrying lumens of the malleable cannula.

7. The apparatus of claim 1, wherein the delivery opening of the tip cap is provided with oval-shaped slit at a distal end thereof.

8. The apparatus of claim 1, wherein the tip cap includes a nipple extending about the delivery opening on a distal surface of the end wall.

9. The apparatus of claim 1, wherein a distal end region of the malleable cannula includes a pair of notches extending from a distal end wall of the malleable cannula to a pair of stop walls axially spaced proximally of the distal end wall, each of the notches exposing a respective semi-cylindrical channel extending from a respective one of the first and second fluid-carrying lumens, and alignment ledges extending laterally from each of the semi-cylindrical channels to an outer perimeter of the malleable cannula.

10. The apparatus of claim 9, wherein the tip insert includes a female mating port complementary to a male projection of the malleable cannula defined by the alignment ledges, the distal end wall, and a portion of the outer perimeter of the malleable cannula extending between the distal end wall and the stop walls.

11. The apparatus of claim 10, wherein the male projection of the malleable cannula further includes a pair of flow path archways, each of the fluid path archways aligning with a respective one of the semi-cylindrical channels when the male projection of the malleable cannula is received in the female mating port, each of the flow path archways providing fluid communication from one of the semi-cylindrical channels to a space between an inner surface of a cylindrical wall of the tip cap and an exterior of the tip insert.

12. The apparatus of claim 1, wherein the malleable cannula has a proximal end region engaging the luer hub sub-assembly, and each of the first and second fluid-carrying lumens being in fluid communication with a respective fluid path hole, a third lumen and a fourth lumen; and
  the spray tip sub-assembly further including a first mixing component from the first fluid-carrying lumen to a first area between the tip cap and the tip insert, a second mixing component from the second fluid-carrying lumen to an a second area between the tip cap and the tip insert, and a combination of the first and second mixing components from both the first and second fluid-carrying lumens to a third area between the tip cap and the tip insert, each of the first, second and third areas being separate from each other, such that there are three fluid paths, each of which enters one of the plurality of feeder channels before mixing, wherein one the three fluid paths is a combination of the first and second mixing components, another is the first mixing component only, and another is the second mixing component only.

13. The apparatus of claim 1, wherein the luer hub sub-assembly includes:
  a proximal hub having a first fluid channel and a second fluid channel;
  a distal hub having a proximal side with a first elongate groove and a second elongate groove therein, each of the first and second elongate recessed channels, together with a distal wall of the proximal hub, defining a respective first and second fluid channel of the distal hub, the first and second fluid channels of the distal hub being in fluid communication with the first fluid channel and second fluid channel, respectively, of the proximal hub, and further including a female cannula-mating port provided on a distal side of the distal hub, wherein the first and second fluid channels of the distal hub terminate at a respective fluid path hole opening to an interior of the cylindrical female cannula-mating port.

14. The apparatus of claim 1, the portion of the tip cap engaging the tip insert including an inwardly-directed registration key of the tip cap received in a complementary alignment notch of the tip insert.

\* \* \* \* \*